(12) United States Patent
Roch et al.

(10) Patent No.: US 7,015,015 B2
(45) Date of Patent: Mar. 21, 2006

(54) HUMAN ENDOSULFINE GENE

(75) Inventors: Jean-Marc Roch, Waukegan, IL (US); Victoria E. S. Scott, Evanston, IL (US); Kristi L. Anderson, Grayslake, IL (US); James P. Sullivan, Deerfield, IL (US)

(73) Assignee: Abbott Laboratories, Abbott Park, IL (US)

( * ) Notice: Subject to any disclaimer, the term of this patent is extended or adjusted under 35 U.S.C. 154(b) by 738 days.

(21) Appl. No.: 09/824,178

(22) Filed: Apr. 2, 2001

(65) Prior Publication Data

US 2002/0142432 A1  Oct. 3, 2002

Related U.S. Application Data

(63) Continuation of application No. 08/779,775, filed on Jan. 7, 1997, now abandoned.

(51) Int. Cl.
*C12N 15/11* (2006.01)
*C12N 5/10* (2006.01)

(52) U.S. Cl. .................. 435/69.1; 435/320.1; 435/325; 536/23.5

(58) Field of Classification Search ................ 536/23.5; 435/69.1, 320.1, 325
See application file for complete search history.

(56) References Cited

PUBLICATIONS

Peyrollier et al. (1996) Biochem. Biophys. Res. Comm. 223: 583–586.*
Hillier et al. (1996) EMBL database AC AA1216133.*
Wallace et al. (1987) Methods in Enzymology 152: 432–442.*
Harlow et al. (1998) Antibodies, A Laboratory Manual. Cold Spring Harbor Laboratory, New York, p. 76.*
Bowie et al. (1987) Science 247: 1307–1310.*

* cited by examiner

*Primary Examiner*—Michael Pak
(74) *Attorney, Agent, or Firm*—Dianne Casuto

(57) ABSTRACT

The present invention provides an isolated or purified polynucleotide that encodes human endosulfine polypeptide. Isoforms of human endosulfine are also disclosed. The invention also provides methods of making recombinant human endosulfine using the polynucleotides and host cells transformed with the polynucleotides.

6 Claims, 9 Drawing Sheets

FIG.2A

```
TGAGCCTTGGGAATAGTTTGGCAGGTTTAACATCCCAAGGCTAACCTAACGTAGTTGGGAAAGGTAG..ATTGAATGAGAGACATGTTTCTGTGCTTCTAA
      ||    ||||  |||   || || | |||||    |||| || ||||||||||||||||||      |||||||||||| ||| |||||| |||||
TTGGTAAAAACATTCCTGACTATCCTTCTTAACCACGTGGCTGATGTGGGGTAGGTATGAGGGGAAGGAAGTGGAGTAGCCTAATGAAAAGGGGTTCTAG

GTGTTCTGTCCCTTAGGCTGCTATTGCTTCATGTTTCCATTATGGCAGGTTTAGAGAA..........TCCTTAAAAAGAAAAATTGACTTGCTTGCCTA
     |||    |||||| |||  |||||    ||||  || |||  |||||| |||             ||||||||| ||||||| |||||| |||
TTGAGCTCTGTAGATAAATGCCTTGTTTCAGTGTGTGTCAGGTGTGGGAGACCTGGTTGGTGTCAGATAAAAGAAACTCCATCCGCACAGACAGATGCAACAGCTCCTCTA

AAACTACAGTGCCCCCTTAGCCTCCATAACTTAGTATCTCTTACAGTTTGCTCTGGCTCTCAAATAATATAAAGATTGATGAACATTATTCACAAAAAAA
   ||  ||||   | | |||   || ||  ||  ||||| ||| ||  ||| |   CTTGAAATAGATTTGCTGTGGGAAGAAGGGCAGTGAGTGTGGGA
GTTCTGCAGAGCTAGTTGAGAACTCAACATTAATCATTTTAAAAAGTACTGTC...CTTGAAATAGATTTGCTGTGGGAAGAAGGGCAGTGAGTGTGGGA

AAAAAAAA............
    |||
GAAAGGAGCCGTGAGCGTGGGGAACCCCACAGAGCCCAAAGGACTTTTTCAGTATTCGAAATAAACAAAACAAAACCCATGAAAAACCCAAAAAAAAA

............
AAAAAAAAA
```

FIG. 2B

```
              1                                                                    50
bov. ARPP19   MSAEVPEAAS AEE....... QKEMEDKVTS PEKAEEAKLK ARYPHLGQKP
bov. endos.                                   EGIL.. PEKAEEAKLK AKYPSLGQKP
hum. endosA   MSQKQEEENP AEETGEEKQD TQEKEGIL.. PEKAEEAKLK AKYPSLGQKP
hum. endosB   MSQKQEEENP AEETGEEKQD TQEKEGIL.. PEKAEEAKLK AKYPSLGQKP
pig endos.                                    EGIL.. PEKAEEAKxx AKYPSLGQKP 51                                                                   100
bov. ARPP19   GGSDFLRKRL QKGQKYFDSG DYNMAKAKMK NKQLPTATPD KTEVTGDHIP
bov. endos.   GGSDFLMKRL QKGQKYFDSG DYNMAKAKMK NKQLPSATPD KNLVTGDHIP
hum. endosA   GGSDFLMKRL QKGQKYFDSG DYNMAKAKMK NKQLPSATPD KNLVTGDHIP
hum. endosB   GGSDFLMKRL QKGQKYFDSG DYNMAKAKMK NKQLPSATPD KNLVTGDHIP
pig endos.    GGSDFLMKRx xxxQKYFDSG DYNMAKxxxx xxQLPSATPD KNLVTGDHIP 101            124
bov. ARPP19   TPQDLPQRKP SLVASKLAG*
bov. endos.   TPQ
hum. endosA   TPQDLPQRKS SLVTSKLAG*
hum. endosB   TPQDLPQRKS SLVTSKLAGG QVE*
pig endos.    TPQDLPQR
```

FIG.3

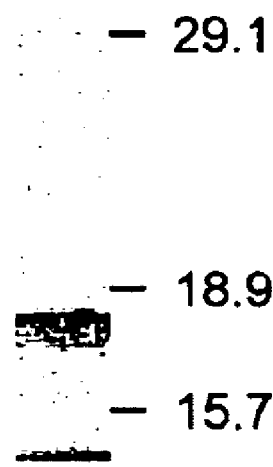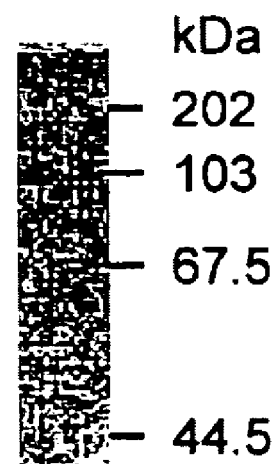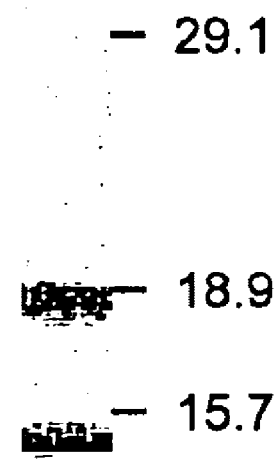
FIG.4A  FIG.4B

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 1103 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO:1:

```
GTGACAGGAG CCGAAGCAGC AGCGCAGGTT GTCCCCGTTT CCCCTCCCCC TTCCCTTCTC      60

CGGTTGCCTT CCCGGGCCCC TTACACTCCA CAGTCCCGGT CCCGCCATGT CCCAGAAACA     120

AGAAGAAGAG AACCCTGCGG AGGAGACCGG CGAGGAGAAG CAGGACACGC AGGAGAAAGA     180

AGGTATTCTG CCTGAGAGAG CTGAAGAGGC AAAGCTAAAG GCCAAATACC CAAGCCTAGG     240
```

-continued

```
ACAAAAGCCT GGAGGCTCCG ACTTCCTCAT GAAGAGACTC CAGAAAGGGC AAAAGTACTT      300

TGACTCAGGA GACTACAACA TGGCCAAAGC CAAGATGAAG AATAAGCAGC TGCCAAGTGC      360

AGGACCAGAC AAGAACCTGG TGACTGGTGA TCACATCCCC ACCCCACAGG ATCTGCCCCA      420

GAGAAAGTCC TCGCTCGTCA CCAGCAAGCT TGCGGGGTAA CCTGAGCCCC CCTCTCCTCC      480

CCTTCCTCAA CCACTGGACG TTTATATATT ATAGGCAGGG ATGAAATGGG CACCTAGTCA      540

GATCTTCTCA GCTTGCTAGC CAGAAATGAC TGTGATTCTG CTGGGGGCTG CTGAGAAGGT      600

AATGTAGGTT GAAAAGGGGC TCTAAGTTTA TTTATTTCGT TAGATTGACA CTTCCACACA      660

CTCCCTGTAG TCCAGGTAGG GCCTAGAAAT AGGAAAGGCT AGGATTGGAT AATGCTGCAA      720

ATGCTTTTTT TGTGTGAGAA ACTGGAGAGA TGTGATTTCT CCTTTTGGGA GAGAATGTCC      780

CAAAATTGAT TAGGCTGAGC CTTGGGAATA GTTTGGCAGG TTTAACATCC CAAGGCTAAC      840

CTAACGTAGT TGGGAAAGGT AGATTGAATG AGACATGTTT TCTGTGCTTC TAAGTGTTCT      900

GTCCCTTAGG CTGCTATTGC TTCATGTTTC CATTATGGCA GGTTTAGAGA ATCCTTAAAA      960

AGAAAAATTG ACTTGCTTGC CTAAAACTAC AGTGCCCCCT TAGCCTCCAT TACTTAGTAT     1020

CTCTTACAGT TTGCTCTGGC TCTCAAATAA TATAAAGATT GATGAACATT ATTCACAAAA     1080

AAAAAAAAAA AAAGGGCGGC GCG                                            1103

(2) INFORMATION FOR SEQ ID NO:2:

(i) SEQUENCE CHARACTERISTICS:
        (A) LENGTH: 1199 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:2:

GTGACAGGAG CCGAAGCAGC AGCGCAGGTT GTCCCCGTTT CCCCTCCCCC TTCCCTTCTC       60

CGGTTGCCTT CCCGGGCCCC TTACACTCCA CAGTCCCGGT CCCGCCATGT CCCAGAAACA      120

AGAAGAAGAG AACCCTGCGG AGGAGACCGG CGAGGAGAAG CAGGACACGC AGGAGAAAGA      180

AGGTATTCTG CCTGAGAGAG CTGAAGAGGC AAAGCTAAAG GCCAAATACC CAAGCCTAGG      240

ACAAAAGCCT GGAGGCTCCG ACTTCCTCAT GAAGAGACTC CAGAAAGGGC AAAAGTACTT      300

TGACTCAGGA GACTACAACA TGGCCAAAGC CAAGATGAAG AATAAGCAGC TGCCAAGTGC      360

AGGACCAGAC AAGAACCTGG TGACTGGTGA TCACATCCCC ACCCCACAGG ATCTGCCCCA      420

GAGAAAGTCC TCGCTCGTCA CCAGCAAGCT TGCGGGTGGC CAAGTTGAAT GATGCTGCCC      480

GGGGCTCTGC CAGATCCTGA GACTGCTTTT GCCGCTTCCC CTCCCTGCCC CACCCGGGTC      540

CTGTGCTGGC TCCTGCCCCT TCAGCCAGGG GTCAGGAGGT GGCTCGGGTG TGGGCTGGAG      600

AGGCAGAAGC CCTTTCCTGT TGGTGTCCCA GCACATGGAG CCCCTTGGGC TGAGCACCAA      660

GACCTTGAAC CTTTTTTGTT TTACCTTTTT TCCAAATAAC AGTTGGGAGA AATATCAATG      720

AAATTCTGGG GGTGGGGGTG GGGCTGAAAG GGTGGGGTGG GAGATATGGA GGAGTATGAA      780

TTAGGGCTTG GAGTTGGTAA AAACATTCCT GACTATCCTT CTTAACCACG TGGCTGATGT      840

GGGGTAGGTA TGAGGGGAAG GAAGTGGAGT AGCCTAATGA AAAGGGGTTC TAGTTGAGCT      900

CTGTAGATAA ATGCCTTGTT TCAGTGTGGT TGGAGACCTG GTGTCAGATA AAAGAAACTC      960

CATCCGCACA GACAGATGCA AACAGCTCCT CTAGTTCTGC AGAGCTAGTT GAGAACTCAA     1020

CATTAATCAT TTTAAAAAGT ACTGTCCTTG AAATAGATTT GCTGTGGGAA GAAGGGCAGT     1080
```

```
GAGTGTGGGA GAAAGGAGCC GTGAGCGTGG GGAACCCCAC AGAGCCCAAA GGACTTTTTC    1140

AGTATTCGAA ATAAACAAAA CAAAAACCCA TGAAAAAACC CAAAAAAAAA AAAAAAAA      1199
```

(2) INFORMATION FOR SEQ ID NO:3:

(i) SEQUENCE CHARACTERISTICS:
        (A) LENGTH: 117 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Met Ser Gln Lys Gln Glu Glu Asn Pro Ala Glu Glu Thr Gly Glu
1               5                   10                  15

Glu Lys Gln Asp Thr Gln Glu Lys Glu Gly Ile Leu Pro Glu Arg Ala
            20                  25                  30

Glu Glu Ala Lys Leu Lys Ala Lys Tyr Pro Ser Leu Gly Gln Lys Pro
        35                  40                  45

Gly Gly Ser Asp Phe Leu Met Lys Arg Leu Gln Lys Gly Gln Lys Tyr
50                  55                  60

Phe Asp Ser Gly Asp Tyr Asn Met Ala Lys Ala Lys Met Lys Asn Lys
65                  70                  75                  80

Gln Leu Pro Ser Ala Gly Pro Asp Lys Asn Leu Val Thr Gly Asp His
                85                  90                  95

Ile Pro Thr Pro Gln Asp Leu Pro Gln Arg Lys Ser Ser Leu Val Thr
                100                 105                 110

Ser Lys Leu Ala Gly
        115
```

(2) INFORMATION FOR SEQ ID NO:4:

(i) SEQUENCE CHARACTERISTICS:
        (A) LENGTH: 121 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Ser Gln Lys Gln Glu Glu Asn Pro Ala Glu Glu Thr Gly Glu
1               5                   10                  15

Glu Lys Gln Asp Thr Gln Glu Lys Glu Gly Ile Leu Pro Glu Arg Ala
            20                  25                  30

Glu Glu Ala Lys Leu Lys Ala Lys Tyr Pro Ser Leu Gly Gln Lys Pro
        35                  40                  45

Gly Gly Ser Asp Phe Leu Met Lys Arg Leu Gln Lys Gly Gln Lys Tyr
50                  55                  60

Phe Asp Ser Gly Asp Tyr Asn Met Ala Lys Ala Lys Met Lys Asn Lys
65                  70                  75                  80

Gln Leu Pro Ser Ala Gly Pro Asp Lys Asn Leu Val Thr Gly Asp His
                85                  90                  95

Ile Pro Thr Pro Gln Asp Leu Pro Gln Arg Lys Ser Ser Leu Val Thr
                100                 105                 110

Ser Lys Leu Ala Gly Gly Gln Val Glu
        115                 120
```

```
(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

GAAGAGACTC CAGAAAGGGC                                              20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

GAAGCAATAG CAGCCTAAGG                                              20

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

TGTGCTGGGA CACCAACAG                                               19

(2) INFORMATION FOR SEQ ID NO:8:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

GGAAGGCGCC ATGTCCCAGA AACAAGAAG                                    29

(2) INFORMATION FOR SEQ ID NO:9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

CAAAGTCGAC TTACCCCGCA AGCTTGCTG                                    29

(2) INFORMATION FOR SEQ ID NO:10:

(i) SEQUENCE CHARACTERISTICS:
        (A) LENGTH: 29 base pairs
```

(B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

CCAAGTCGAC TCATTCAACT TGGCCACCC                                         29

(2) INFORMATION FOR SEQ ID NO:11:

(i) SEQUENCE CHARACTERISTICS:
        (A) LENGTH: 111 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Met Ser Ala Glu Val Pro Glu Ala Ala Ser Ala Glu Glu Gln Lys Glu
1               5                   10                  15

Met Glu Asp Lys Val Thr Pro Glu Lys Ala Glu Glu Ala Lys Leu Lys
            20                  25                  30

Ala Arg Tyr Pro His Leu Gly Gln Lys Pro Gly Gly Ser Asp Phe Leu
        35                  40                  45

Arg Lys Arg Leu Gln Lys Gly Gln Lys Tyr Phe Asp Ser Gly Asp Tyr
    50                  55                  60

Asn Met Ala Lys Ala Lys Met Lys Asn Lys Gln Leu Pro Thr Ala Thr
65                  70                  75                  80

Pro Asp Lys Thr Glu Val Thr Gly Asp His Ile Pro Thr Pro Gln Asp
                85                  90                  95

Leu Pro Gln Arg Lys Pro Ser Leu Val Arg Ser Lys Leu Ala Gly
            100                 105                 110

(2) INFORMATION FOR SEQ ID NO:12:

(i) SEQUENCE CHARACTERISTICS:
        (A) LENGTH: 77 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

Glu Gly Ile Leu Pro Glu Arg Ala Glu Glu Ala Lys Leu Lys Ala Lys
1               5                   10                  15

Tyr Pro Ser Leu Gly Gln Lys Pro Gly Gly Ser Asp Phe Leu Met Lys
            20                  25                  30

Arg Leu Gln Lys Gly Gln Lys Tyr Phe Asp Ser Gly Asp Tyr Asn Met
        35                  40                  45

Ala Lys Ala Lys Met Lys Asn Lys Gln Leu Pro Ser Ala Gly Pro Asp
    50                  55                  60

Lys Asn Leu Val Thr Gly Asp His Ile Pro Thr Pro Gln
65                  70                  75

(2) INFORMATION FOR SEQ ID NO:13:

(i) SEQUENCE CHARACTERISTICS:
        (A) LENGTH: 82 amino acids
        (B) TYPE: amino acid
        (C) STRANDEDNESS: single -continued (D) TOPOLOGY: linear (ii) MOLECULE TYPE: protein (xi) SEQUENCE DESCRIPTION: SEQ ID NO:13:

```
Glu Gly Ile Leu Pro Glu Arg Ala Glu Glu Ala Lys Xaa Xaa Ala Lys
1               5                   10                  15

Tyr Pro Ser Leu Gly Gln Lys Pro Gly Gly Ser Asp Phe Leu Met Lys
            20                  25                  30

Arg Xaa Xaa Xaa Xaa Gln Lys Tyr Phe Asp Ser Gly Asp Tyr Asn Met
        35                  40                  45

Ala Lys Xaa Xaa Xaa Xaa Xaa Xaa Gln Leu Pro Ser Ala Gly Pro Asp
    50                  55                  60

Lys Asn Leu Val Thr Gly Asp His Ile Pro Thr Pro Gln Asp Leu Pro
65                  70                  75                  80

Gln Arg
```

HUMAN ENDOSULFINE GENE

This is a continuation of application Ser. No. 08/779,775 filed Jan. 7, 1997, now abandoned.

TECHNICAL FIELD

The invention relates generally to polynucleotide sequences and polypeptide sequences encoded therein, as well as methods which utilize these sequences for detecting endosulfines in human tissues.

BACKGROUND OF THE INVENTION

ATP-sensitive potassium channels ($K^+$ channels), which represent a family of potassium channels inhibited by intracellular ATP, have been found in a variety of tissues including heart, pancreatic beta-cells, skeletal muscle, smooth muscle and the central nervous system (G. Edwards and A. H. Weston, *Ann. Rev. Pharmacol. Toxicol.* 33: 597–637 (1993)). These ATP-sensitive $K^+$ channels have been associated with diverse cellular functions, such as shortening of action potential duration and cellular loss of potassium ions that occur during metabolic inhibition in heart, smooth muscle relaxation, regulation of skeletal muscle excitability, and neurotransmitter release (A. Terzic, et al., *Am. J. Physiol.* 269: C525–C545 (1995)).

For example, in pancreatic beta-cells (β-cells), ATP-sensitive $K^+$ channels play an important role in linking the metabolic status of the cell to cellular excitability. The primary physiological stimulus for insulin secretion is a rise in blood glucose concentrations. Glucose enters the beta-cell where it is metabolized resulting in elevated intracellular ATP and a concomitant lowering of intracellular ADP. These changes in nucleotide levels act synergistically to close ATP-sensitive $K^+$ channels in the plasma membrane, because ATP inhibits whereas ADP activates channel activity. The closure of ATP-sensitive $K^+$ channels causes a membrane depolarization that opens voltage dependent calcium channels and triggers electrical activity. The calcium influx that ensues raises intracellular calcium and stimulates insulin secretion (F. M. Ashcroft, *Nature Medicine,* 2: 1301–1302 (1996)). Recently, it has been shown that the ATP-sensitive $K^+$ channel in pancreas is a complex composed of at least two subunits, a channel forming subunit (Kir 6.2) that selectively conducts potassium and a regulatory protein termed the sulfonylurea receptor (SUR1) (N. Inagaki, et al., *Science* 270: 1166–1170). Co-expression of these two subunits constituted inwardly rectifying ATP-sensitive $K^+$ channels with expected pharmacological and biophysical properties.

An emerging diversity of ATP-sensitive $K^+$ channels is now known to exist. Two channel forming subunits (Kir 6.1 and Kir 6.2) and three regulatory subunits (SUR 1, SUR 2A and SUR 2B) have recently been cloned from mammalian tissues (S. Isomoto, et al., *Neuron* 16: 1011–1017 (1996)). The elucidation of this molecular diversity supports earlier pharmacological studies demonstrating that ATP-sensitive $K^+$ channels in different tissues exhibit considerable variation in response to activators and inhibitors (G. Edwards, supra).

ATP-sensitive potassium channels are the molecular targets for two important classes of drugs, the sulfonylureas and the $K^+$ channel openers. Sulfonylureas are widely used in the management of non-insulin dependent diabetes mellitus (NIDDM), a disease characterized by decreased insulin content and impaired response to glucose (H. E. Lebovitz, in *Diabetes Mellitus: Theory and Practice,* eds. H. Rifkin, & D. Porte, Jr. (Elsevier, N.Y.), pp.554–574 (1990)). In the pancreas, sulfonylurea drugs stimulate insulin secretion in the islets of Langerhans, which have partially lost their sensitivity to glucose (E. Cerasi, et al., *Diabetes* 21: 224–234 (1972)). This class of drugs inhibits ATP-sensitive $K^+$ channel opening through an interaction with the regulatory subunit (SUR 1) of the pancreatic β-cell ATP-sensitive $K^+$ channel and thereby stimulate insulin release (E. Cerasi, et al., *Diabetes* 21: 224–234 (1972)).

The biological effects of sulfonylurea drugs led Virsolvy-Vergine, et al. to postulate the existence of an endogenous ligand for sulfonylurea receptors (A. Virsolvy-Vergine, et al., *FEBS Lett.* 242: 65–69 (1988)). Later they identified a peptide from ovine brain, which was shown to bind receptors from both the central nervous system (CNS) and pancreatic β cells and to induce insulin secretion from a rodent beta-cell tumor line (βTC cells) in vitro. They concluded that this peptide is a natural ligand for the sulfonylurea receptor and may play a role in the normal physiology of the CNS and pancreas. They termed this peptide "endosulfine" (A. Virsolvy-Vergine, et al., *Proc. Natl. Acad. Sci. USA* 89: 6629–6633 (1992)).

The complete amino acid or nucleotide sequence of endosulfine has not been determined in any species; partial cDNA sequence has recently been obtained from bovine tissue (K. Peyrollier, et al., *Biochem. Biophys. Res. Comm.* 223: 583–586 (1996)). No information on the nucleotide or amino acid sequence of human endosulfine has been reported. The emerging molecular diversity of ATP-senstive $K^+$ channels raises the possibility that a family of endosulfine molecules may exist, that display tissue specific expression and differentially interact with SUR isoforms.

The reported effects of bovine and ovine endosulfine to interact with sulfonylurea receptors and modulate insulin release suggests that the isolation and characterization of a family of human endosulfines offers the potential to develop new therapeutic and diagnostic agents for the treatment of disease states. Such therapeutics may include recombinant endosulfine, antisense deoxyribonucleotides, transcriptional regulators and activators or inhibitors of endosulfine activity. For example, human endosulfine or modulators of endosulfine activity may represent an alternative approach to the treatment of diabetes if a human endosulfine is found to modulate insulin levels as has been reported for ovine endosulfine (A. Virsolvy-Vergine, et al., (1992) supra). Furthermore, in the CNS, where ATP-sensitive $K^+$ channels modulate neuronal excitability, modulators of endosulfine may represent a target for the treatment of disease involving abnormal neuronal firing such as epilepsy, pain, depression and ischemia. In heart, where SUR 2A is selectively expressed and ATP-sensitive $K^+$ channels play a role in control of action potential duration, modulation of endosulfine levels and/or activity may represent an approach to the treatment of cardiac ischemia. ATP-sensitive $K^+$ channels expressed in skeletal muscle alter the electrical activity of the cells in response to changes in energy status and modulation of this complex with $K^+$ channel openers has proven beneficial in a number of disease states including myotonia congita and for patients with hypokalemic paralysis (A. C. Wareham, in *Potassium Channel Modulators: Pharmacological, Molecular and Clinical Aspects:* eds. A. H. Weston, and T. C. Hamilton, pp. 110–143 (1992)). However in this case, the side effects of the compounds precludes their widespread use. An endosulfine selectively expressed in skeletal muscle may offer an alternative approach to normalizing skeletal muscle excitability and thus may be utilized in a number of skeletal muscle disorders. Therefore, it would be advantageous to isolate of a DNA sequence encoding a full length human endosulfine which would permit investigation of its use toward the development of therapeutics.

Mutations in SUR1 and Kir 6.2 have been linked to persistant hyperinsulinemic hypoglycernia of infancy (PHHI) (P. M. Thomas, et al. *Science* 268: 426–429 (1995) and P. Thomas, et al., *Hum. Mol. Gen.* 5: 1809–1812 (1996)) and a recent report has suggested that mutations in SUR1 may also be linked to non-insulin dependent diabetes (H. Inoue, et al., *Diabetes* 45: 825–831, (1996)). The isolation and characterization of a human endosulfine will facilitate studies to determine if mutations exist in the endosulfine gene, if such mutations result in altered expression and/or activity of the protein and if these mutations are linked to disease states such as diabetes, epilepsy, depression and ischemia. The ability to identify normal and mutated forms of endosulfine in human cells would then offer the opportunity to develop diagnostic tests for such disease states.

Thus, it would be advantageous to provide specific methods and reagents for the diagnosis, staging, prognosis, monitoring, prevention or treatment of diseases and conditions associated with abnormal regulation or expression of human endosulfine or to indicate possible predisposition to these conditions.

SUMMARY OF THE INVENTION

The present invention provides an isolated or purified polynucleotide comprising a nucleotide sequence which encodes a human endosulfine and fragments or compliments thereof. Preferably, the nucleotide sequence is selected from the group consisting of SEQ ID NO:1 and SEQ ID NO:2 or fragments thereof. More preferably, the nucleotide sequence is SEQ ID NO:1 from about nucleotide position 107 to about nucleotide position 460 or SEQ ID NO:2 about nucleotide position 107 to about nucleotide position 472. The invention further provides a polynucleotide comprising a nucleotide sequence which encodes a human endosulfine having the sequence of SEQ ID NO:3 or SEQ ID NO:4.

In another aspect, the polynucleotide can be produced by recombinant techniques. A recombinant molecule comprises a nucleotide sequence that encodes a human endosulfine and is contained within an expression vector. The expression vector may be either a prokaryotic or a eukaryotic vector. Preferred expression vectors are pProEx1 and pcDNA3.1. In a more preferred embodiment, the nucleotide sequence which encodes a human endosulfine has the sequence SEQ ID NO:1 from about nucleotide position 107 to about nucleotide position 460 or the sequence SEQ ID NO:2 from about nucleotide position 107 to about nucleotide position 472.

The present invention further provides a host cell transformed with said vector. The host cell is either a prokaryotic or eukaryotic cell.

The present invention also provides a polypeptide of a human endosulfine or fragments thereof. In a preferred embodiment, the polypeptide has the amino acid sequence SEQ ID NO:3 or SEQ ID NO:4. The polypeptide can be produced by recombinant technology and provided in purified form.

In another aspect, the invention provides a method for producing a polypeptide which contains at least one human endosulfine epitope, wherein the method comprises incubating host cells transformed with an expression vector comprising a nucleotide sequence which encodes a human endosulfine. Preferably, the expression vector comprises a nucleotide sequence having the sequence SEQ ID NO:1 or SEQ ID NO:2 and fragments and compliments thereof. More preferably, the nucleotide sequence has the sequence SEQ ID NO:1 from about nucleotide position 107 to about nucleotide position 460 or SEQ ID NO:2 from about nucleotide position 107 to about nucleotide position 472. Even more preferably, the nucleotide sequence encodes a human endosulfine having sequence SEQ ID NO:3 or SEQ ID NO:4.

In another aspect, the invention provides a method for identifying compounds that modulate endosulfine receptor activity, comprising the steps of: (a) providing a host cell that expresses the endosulfine receptor polypeptide; (b) mixing a test compound with the cell; and (c) measuring either (i) the effect of the test compound on the cell expressing the receptor, or (ii) the binding of the test compound to the cell or to the receptor. The host cell of the method is either a prokaryotic or eukaryotic cell. Preferably in the method, the measurement of step (c)(ii) is performed by measuring a signal generated by a signal generating compound or by measuring a signal generated by a radiolabeled ion, a fluorescent probe or an electrical current.

In yet another aspect, the invention provides a method for identifying a cytoprotective compound, comprising the steps of: (a) providing a cell that expresses an endosulfine polypeptide or fragment thereof; (b) combining a test compound with the cell; and (c) monitoring the cell or cellular function for an indication of cytotoxicity. The host cell of the method is either a prokaryotic or eukaryotic cell. Preferably, the method comprises providing a cell which has an expression vector comprising a polynucleotide having the nucleotide sequence SEQ ID NO:2 from about nucleotide position 107 to about nucleotide position 472 operably linked to control sequences that direct the transcription of the polynucleotide whereby the polynucleotide is expressed in a host cell. More preferably, one of the control sequences comprises an inducible promotor. Even more preferably, the cell is maintained in the presence of a substance which minimizes or blocks a cytotoxic effect on the cell.

In yet another aspect, the invention provides a method of treating an individual having a condition associated with endosulfine modulation, comprising administering to the individual an effective amount of a compound that controls the gene expression of endosulfine, in a pharmaceutically acceptable excipient.

In yet another embodiment, the invention provides a monoclonal antibody which specifically binds to human endosulfine having amino acid sequence SEQ ID NO:4 or fragments thereof.

BRIEF DESCRIPTION OF THE DRAWINGS

FIG. 2 shows the alignment (GAP Program, Wisconsin Sequence Analysis Package, Version 8, Genetics Computer Group, Madison, Wis.) between cDNA sequences of endosulfine A (top line, SEQ ID NO:1) and endosulfine B (bottom line, SEQ ID NO:2). Vertical lines between the two sequences indicate identical nucleotides at those positions. Methionine initiation codons (ATG) and stop codons (TAA in top strand and TGA in bottom strand) are shown in bold type and are underlined.

FIG. 3 shows the comparative bestfit analysis between amino acid sequences of a bovine cAMP-regulated phosphoprotein of $M_r$=19,000 (bov. ARPP19, SEQ ID NO:11), bovine endosulfine (bov. endos., SEQ ID NO:12), porcine endosulfine (pig endos., SEQ ID NO:13), human endosulfine A (hum. endosA, SEQ ID NO:3) and human endosulfine B (hum. endosB, SEQ ID NO:4). The porcine endosulfine sequence was generated by aligning four partial sequences obtained from A. Virsolvy-Vergine, et al. (1996) supra with the amino acid sequence of bovine ARPP-19 and filling in gaps with the letter "x" (wherein x represents an unknown amino acid). Dots represent spaces which are placed within the sequence in order to generate the best alignment.

FIG. 4 shows an autoradiogram of [$^{35}$S]-labeled endosulfines generated from clone 700415 (lane A) and clone 384387 (lane B) in an in vitro transcription/translation system (Promega, Madison, Wis.). Prior to autoradiography, proteins were resolved by SDS-PAGE on a 10% polyacrylamide gel. Molecular weight sizes are indicated at the side of lane B.

Figure 1:
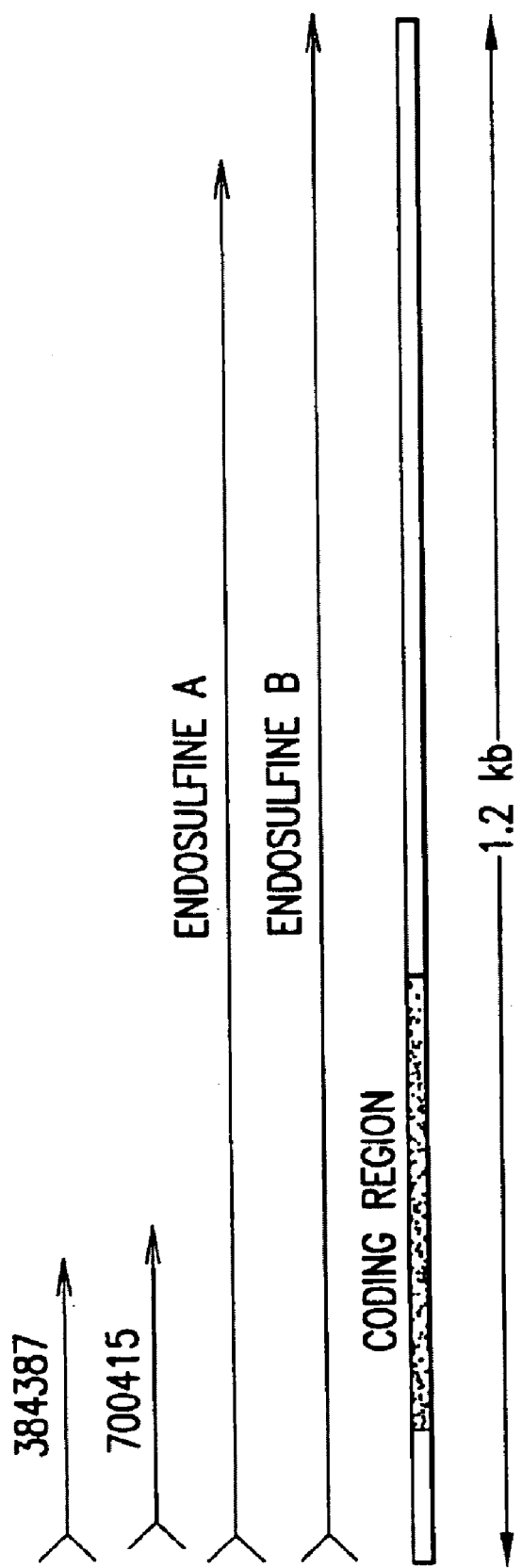
FIG. 1 shows diagrammatically the position of the Expressed Sequence Tags (ESTs) for clones 384387 and 700415 with respect to the coding regions of the endosulfine A and endosulfine B genes.

The right panel shows PCR products obtained using cDNAs generated from human poly A$^+$ RNA prepared from brain (lanes 1 and 6), cerebellum (lanes 2 and 7), fetal brain (lanes 3 and 8), pancreas (lanes 4 and 9) and substantia nigra (lanes 5 and 10) as templates with primer pairs SEQ ID NO:5/SEQ ID NO:6 (lanes 1–5) and SEQ ID NO:5/SEQ ID NO:7 (lanes 6–10).

Figure 7:
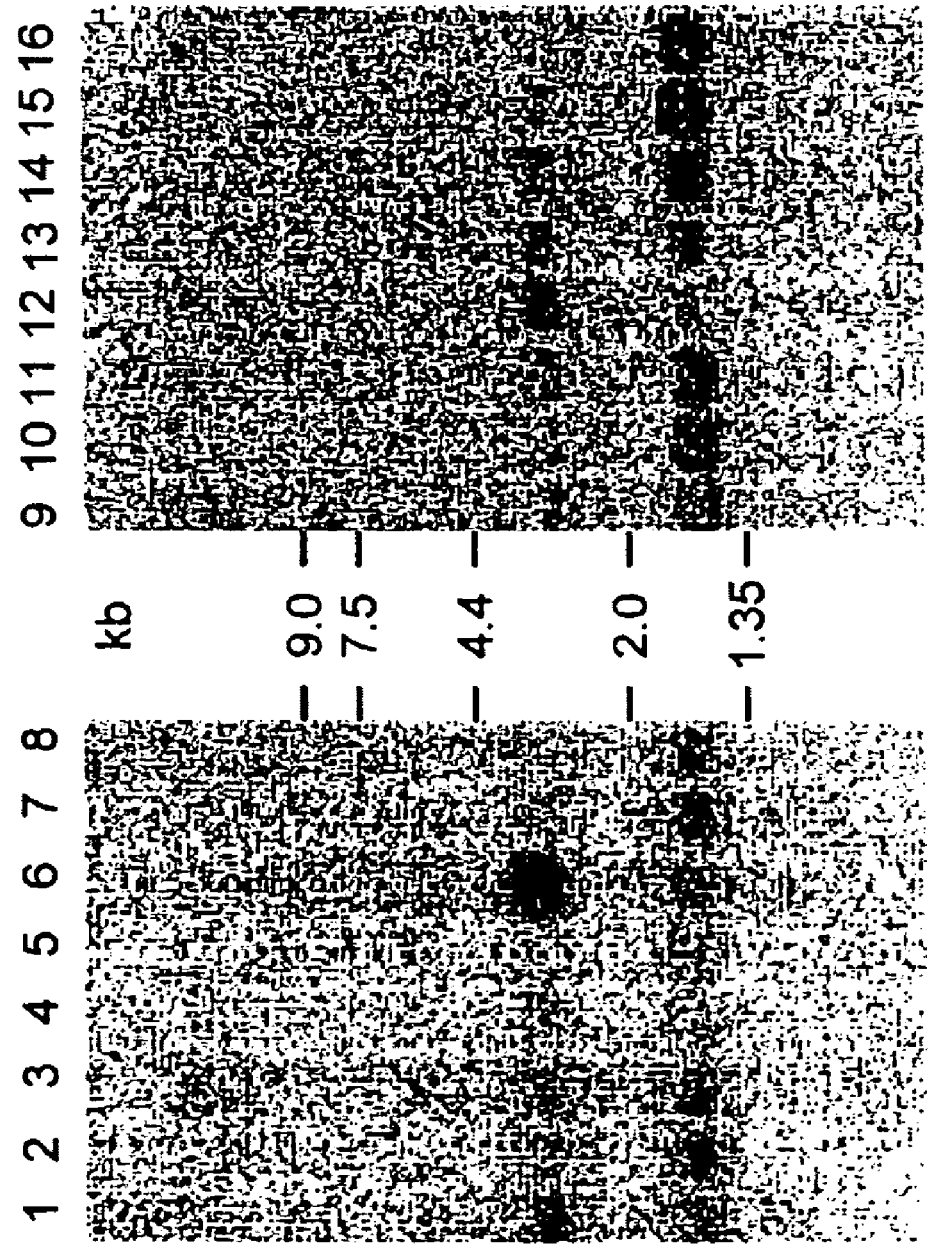

FIG. 7 shows computer generated images of Northern blots of poly A$^+$ RNA isolated from human heart (lane 1), brain (lane 2), placenta (lane 3), lung (lane 4), liver (lane 5), skeletal muscle (lane 6), kidney (lane 7), pancreas (lane 8), spleen (lane 9), thymus (lane 10), prostate (lane 11), testis (lane 12), ovary (lane 13), small intestine (lane 14), colon (lane 15), and leukocytes (lane 16) and probed with a 190 bp DNA fragment of the 5'-untranslated region (5'-UTR) of endosulfines A and B (i.e. SEQ ID NO:1 or SEQ ID NO:2 from nucleotide position 1 to nucleotide position 190). Molecular weight markers are shown at the sides of each panel.

Figure 8:
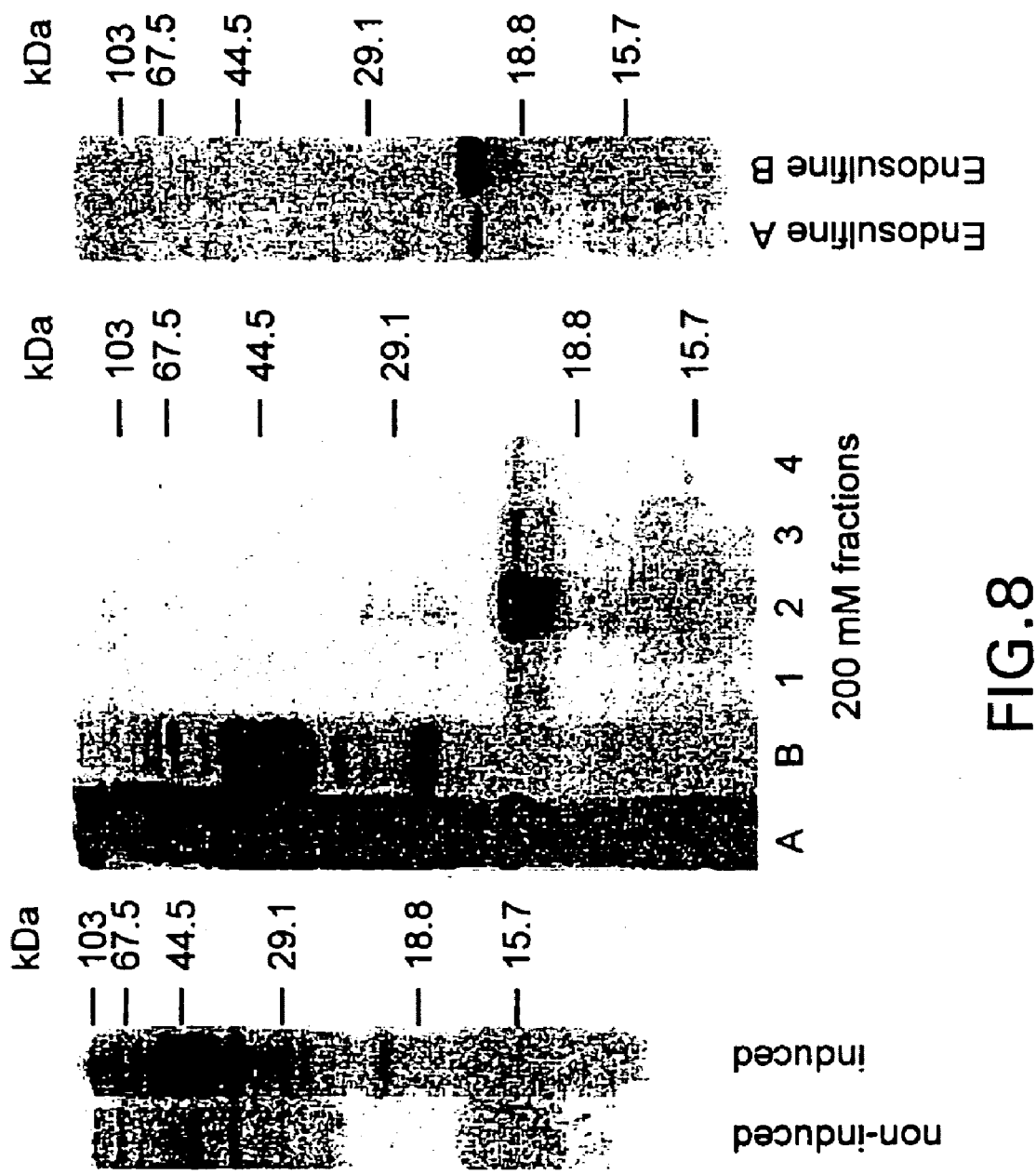

FIG. 8 shows computer generated images of proteins from bacterial lysates (left panel), purified his-tagged endosulfine B (center panel) and purified his-tagged endosulfines A and B (right panel) resolved by SDS PAGE on 13.5% gels and stained with Coumassie blue. The left panel shows proteins of bacterial lysates prepared from DH5α cells tranformed with a pProEx 1 expression vector comprising human endosulfine B cDNA, grown in Luria broth+ampicillin and either induced or not induced with IPTG during growth of the cells. A dark band representing his-tagged human endosulfine B is visable immediately above the 18.8 kDA molecular weight marker. The right panel shows purified his-tagged endosulfines A and B.

Purification of the fusion protein from the total bacterial lysate by Ni-NTA affinity chromatography is shown on the gel in the center panel. Total lysate was applied to an Ni-NTA column, washed with buffer containing 50 mM imidazole and eluted with buffer containing 0.2 M imidazole. Lane A: Proteins from total bacterial lysate; lane B: proteins from 50 mM imidazole wash buffer; lanes 1–4: proteins from fractions eluted with 0.2 M imidazole buffer. Molecular weight markers are shown at the sides of each panel. The right panel

DETAILED DESCRIPTION OF THE INVENTION

The present invention provides isolated and purified polynucleotides that encode a human endosulfine, fragments thereof, expression vectors containing those polynucleotides, host cells transformed with those expression vectors, a process for making a human endosulfine using those polynucleotides and vectors, and isolated and purified recombinant human endosulfine and polypeptide fragments thereof.

The present invention also provides methods for assaying a test sample for products of a human endosulfine gene, which comprises making cDNA from mRNA in the test sample, and detecting the cDNA as an indication of the presence of a human endosulfine gene. The method may include an amplification step, wherein portions of the cDNA corresponding to the gene or fragment thereof is amplified. Methods also are provided for assaying for the translation products of mRNAs. Test samples which may be assayed by the methods provided herein include tissues, cells, body fluids and secretions. The present invention also provides reagents such as oligonucleotide primers and polypeptides which are useful in performing these methods.

Portions of the nucleic acid sequences disclosed herein are useful as primers for the reverse transcription of RNA or for the amplification of cDNA; or as probes to determine the presence of certain cDNA sequences in test samples. Also disclosed are nucleic acid sequences which permit the production of encoded polypeptide sequences which are useful as standards or reagents in diagnostic immunoassays, targets for pharmaceutical screening assays and/or as components or target sites for various therapies. Monoclonal and polyclonal antibodies directed against at least one epitope contained within these polypeptide sequences are useful for diagnostic tests and for screening for diseases or conditions associated with abnormal endosulfine production. Isolation of sequences from other portions of the gene of interest can be accomplished by utilizing probes or PCR primers derived from these nucleic acid sequences, thus allowing additional probes and polypeptides of the genome of interest to be established.

The techniques for determining the amino acid sequence "similarity" are well-known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. The techniques for determining nucleic acid and amino acid sequence identity also are well known in the art and include determining the nucleotide sequence of the mRNA for that gene (usually via a cDNA intermediate) and determining the amino acid sequence encoded therein, and comparing this to a second amino acid sequence. In general, "identity" refers to an exact nucleotide to nucleotide or amino acid to amino acid correspondence of two polynucleotides or polypeptide sequences, respectively. Two or more polynucleotide sequences can be compared by determining their "percent identity." Two amino acid sequences likewise can be compared by determining their "percent identity." For example, a polypeptide or amino acid sequence may preferably have about 90% identity and most preferably about 95% identity to an amino acid sequence of a human endosulfine. Further, the polypeptide or amino acid sequence may preferably have at least about 85% similarity, more preferably about 90% similarity and most preferably about 95% similarity to a polypeptide or amino acid sequence of a human endosulfine. The programs available in the Wisconsin Sequence Analysis Package, Version 8 (available from Genetics Computer Group, Madison, Wis.), for example, the GAP program, are capable of calculating both the identity between two polynucleotides and the identity and similarity between two polypeptide sequences, respectively. Other programs for calculating identity or similarity between sequences are known in the art.

Although the physiological manifestions of abnormal endosulfine expression are as yet unknown in humans or other mammals, we postulate that endosulfine may play a pathological role resulting from its abnormal expression. For example, Virsolvy-Vergine et al. (1992) op cit. have postulated that poor expression and/or secretion of endosulfine in the pancreas may be associated with NIDDM pathology and in the brain, with cerebral ischemia. It is also reasonable to postulate that the presence of endosulfine in certain body fluids where it is not normally found may be indicative of a disease state, the further progression of which could be monitored by assaying for endosulfine in such fluids. A similar role is seen for myelin basic protein (MBP) which in the normal physiological state is a membrane bound protein and therefore not found in body fluids, but in disease states such as multiple sclerosis, it is released into cerebral spinal fluid. Furthermore, the presence of a polynucleotide or fragment thereof which encodes endosulfine in tissues or body fluids where it is unexpected, may also be indicative of a disease condition, in the case, for example, where the disease was manifest by cellular degeneration.

Thus, the reagents and methods described herein may enable the identification of certain markers as indicative of abnormal endosulfine expression and the information obtained therefrom may aid in the diagnosis, staging, monitoring, prognosis and/or therapy of diseases or conditions which may be associated with such expression. Test methods include, for example, probe assays which utilize the sequence(s) provided herein and which also may utilize nucleic acid amplification methods such as the polymerase chain reaction (PCR), the ligase chain reaction (LCR); and hybridization. In addition, the nucleotide sequences provided herein contain open reading frames from which an immunogenic epitope may be found. Preferably, such an epitope is unique to the disease state or condition associated with the endosulfine gene. The uniqueness of the epitope may be determined by its immunological reactivity with the polypeptide product encoded by such gene, and lack of immunological reactivity with tissue(s) from non-diseased patients. Methods for determining immunological reactivity are well-known and include but are not limited to, for example, radioimmunoassay (RIA), enzyme-linked immunosorbent assay (ELISA), hemagglutination (HA), fluorescence polarization immunoassay (FPIA); chemiluminescent immunoassay (CLIA), and others; several examples of suitable methods are described herein.

Definitions

Unless otherwise stated, the following terms shall have the following meanings:

A polynucleotide "derived from" a designated sequence refers to a polynucleotide sequence which is comprised of a sequence of approximately at least about 6 nucleotides, is preferably at least about 8 nucleotides, is more preferably at least about 10–12 nucleotides, and even more preferably is at least about 15–20 nucleotides corresponding, i.e., identical to or complementary to, a region of the designated nucleotide sequence. The sequence may be complementary to or identical to a sequence which is unique to a particular polynucleotide sequence as determined by techniques known in the art. Comparisons to sequences in databanks, for example, can be used as a method to surmise the uniqueness of a designated sequence. Regions from which sequences may be derived include but are not limited to regions encoding specific epitopes, as well as non-translated and/or non-transcribed regions.

The derived polynucleotide will not necessarily be derived physically from the nucleotide sequence of interest under study, but may be generated in any manner, including but not limited to chemical synthesis, replication, reverse transcription or transcription, which is based on the information provided by the sequence of bases in the region(s) from which the polynucleotide is derived; as such, it may represent either a sense or an antisense orientation of the original polynucleotide. In addition, combinations of regions corresponding to that of the designated sequence may be modified in ways known in the art to be consistent with an intended use.

The term "probe" denotes a defined nucleic acid segment (or nucleotide analog segment, i.e., peptide nucleic acid analog (PNA) or morpholino analog (MA) which can be used to identify specific DNA or RNA present in samples bearing the complementary sequence.

The term "primer" denotes a specific oligonucleotide sequence complementary to a target nucleotide sequence and used to hybridize to the target nucleotide sequence and serve as an initiation point for nucleotide polymerization catalyzed by either DNA polymerase or reverse transcriptase.

A "polypeptide" or "amino acid" sequence derived from a designated nucleic acid sequence refers to a polypeptide having an amino acid sequence identical to that of a polypeptide encoded in the sequence or a portion thereof wherein the portion consists of at least 3 to 5 amino acids, and more preferably at least 8 to 10 amino acids, and even more preferably 15 to 20 amino acids, or which is immunologically identifiable with a polypeptide encoded in the sequence.

A "recombinant polypeptide" as used herein means at least a polypeptide which by virtue of its origin or manipulation is not associated with all or a portion of the polypeptide with which it is associated in nature and/or is linked to a polypeptide other than that to which it is linked in nature. A recombinant or derived polypeptide is not necessarily translated from a designated nucleic acid sequence. It also may be generated in any manner, including chemical synthesis or expression of a recombinant expression system.

The term "synthetic peptide" as used herein means a polymeric form of amino acids of any length, which may be chemically synthesized by methods well-known to the routineer. These synthetic peptides are useful in various applications.

The term "polynucleotide" as used herein means a polymeric form of nucleotides of any length, either ribonucleotides or deoxyribonucleotides. This term refers only to the primary structure of the molecule. Thus, the term includes double- and single-stranded DNA, as well as, double- and single-stranded RNA. It also includes modifications, such as methylation or capping, and unmodified forms of the polynucleotide.

"A sequence corresponding to a cDNA" means that the sequence contains a polynucleotide sequence that is identical to or complementary to a sequence in the designated DNA. The degree (or "percent") of identity or complementarity to the cDNA will be approximately 50% or greater, will preferably be at least about 70% or greater, and more preferably will be at least about 90% or greater. The sequence that corresponds will be at least about 50 nucleotides in length, will preferably be about 60 nucleotides in length, and more preferably, will be at least about 70 nucleotides in length. The correspondence between the gene or gene fragment of interest and the cDNA can be determined by methods known in the art, and include, for example, a direct comparison of the sequenced material with the cDNAs described, or hybridization and digestion with single strand nucleases, followed by size determination of the digested fragments.

"Purified polynucleotide" refers to a polynucleotide of interest or fragment thereof which is essentially free, i.e., contains less than about 50%, preferably less than about 70%, and more preferably, less than about 90% of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density. Thus, "purified polypeptide" means a polypeptide of interest or fragment thereof which is essentially free, that is, contains less than about 50%, preferably less than about 70%, and more preferably, less than about 90% of cellular components with which the polypeptide of interest is naturally associated. Methods for purifying are known in the art.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, which is separated from some or all of the coexisting materials in the natural system, is isolated. Such polynucleotide could be part of a vector and/or such polynucleotide or polypeptide could be part of a composition, and still be isolated in that the vector or composition is not part of its natural environment.

"Polypeptide" as used herein indicates a molecular chain of amino acids and does not refer to a specific length of the product. Thus, peptides, oligopeptides and proteins are included within the definition of polypeptide. This term, however, is not intended to refer to post-expression modifications of the polypeptide, for example, glycosylations, acetylations, phosphorylations and the like.

"Recombinant host cells," "host cells," "cells," "cell lines," "cell cultures," and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

As used herein "replicon" means any genetic element, such as a plasmid, a chromosome or a virus, that behaves as an autonomous unit of polynucleotide replication within a cell.

A "vector" is a replicon in which another polynucleotide segment is attached, such as to bring about the replication and/or expression of the attached segment.

The term "control sequence" refers to polynucleotide sequences which are necessary to effect the expression of coding sequences to which they are ligated. The nature of such control sequences differs depending upon the host organism. In prokaryotes, such control sequences generally include promoter, ribosomal binding site and terminators; in eukaryotes, such control sequences generally include promoters, terminators and, in some instances, enhancers. The term "control sequence" thus is intended to include at a minimum all components whose presence is necessary for expression, and also may include additional components whose presence is advantageous, for example, leader sequences.

"Operably linked" refers to a situation wherein the components described are in a relationship permitting them to function in their intended manner. Thus, for example, a control sequence "operably linked" to a coding sequence is ligated in such a manner that expression of the coding sequence is achieved under conditions compatible with the control sequences.

The term "open reading frame" or "ORF" refers to a region of a polynucleotide sequence which encodes a polypeptide; this region may represent a portion of a coding sequence or a total coding sequence.

A "coding sequence" is a polynucleotide sequence which is transcribed into mRNA and translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences.

The term "immunologically identifiable with/as" refers to the presence of epitope(s) and polypeptide(s) which also are present in and are unique to the designated polypeptide(s). Immunological identity may be determined by antibody binding and/or competition in binding. These techniques are known to the routineer and also are described herein. The uniqueness of an epitope also can be surmised by computer searches of known data banks, such as GenBank, for the polynucleotide sequences which encode the epitope, and by amino acid sequence comparisons with other known proteins.

As used herein, "epitope" means an antigenic determinant of a polypeptide. Conceivably, an epitope can comprise three amino acids in a spatial conformation which is unique to the epitope. Generally, an epitope consists of at least five such amino acids, and more usually, it consists of at least eight to ten amino acids. Methods of examining spatial conformation are known in the art and include, for example, x-ray crystallography and two-dimensional nuclear magnetic resonance.

A "conformational epitope" is an epitope that is comprised of specific juxtaposition of amino acids in an immunologically recognizable structure, such amino acids being present on the same polypeptide in a contiguous or non-contiguous order or present on different polypeptides.

A polypeptide is "immunologically reactive" with an antibody when it binds to an antibody due to antibody recognition of a specific epitope contained within the polypeptide. Immunological reactivity may be determined by antibody binding, more particularly by the kinetics of antibody binding, and/or by competition in binding using as competitor(s) a known polypeptide(s) containing an epitope against which the antibody is directed. The methods for determining whether a polypeptide is immunologically reactive with an antibody are known in the art.

As used herein, the term "immunogenic polypeptide containing an epitope of interest" means naturally occurring polypeptides of interest or fragments thereof, as well as polypeptides prepared by other means, for example, by chemical synthesis or the expression of the polypeptide in a recombinant organism.

The terms "transformation" refers to the insertion of an exogenous polynucleotide into a prokaryotic or yeast host cell, irrespective of the method used for the insertion. Generally, the term "transfection" is used with respect to insertion of an exogenous polynucleotide into a eukaryotic host cell. The processes for achieving transformation and/or transfection are well known to those of ordinary skill in the art and include such techniques as direct uptake, transduction, f-mating and electroporation. The exogenous polynucleotide may be maintained as a non-integrated vector, for example, a plasmid, or alternatively, may be integrated into the host genome.

"Treatment" refers to prophylaxis and/or therapy.

The term "individual" as used herein refers to vertebrates, particularly members of the mammalian species and includes but is not limited to domestic animals, sports animals, primates and humans; more particularly the term refers to humans.

The term "sense strand" or "plus strand" (or "+") as used herein denotes a nucleic acid that contains the sequence that encodes the polypeptide. The term "antisense strand" or "minus strand" (or "−") denotes a nucleic acid that contains a sequence that is complementary to that of the "plus" strand.

The term "test sample" refers to a component of an individual's body which is the source of the analyte (such as, antibodies of interest or antigens of interest). These components are well known in the art. These test samples include biological samples which can be tested by the methods of the present invention described herein and include human and animal body fluids such as whole blood, serum, plasma, cerebrospinal fluid, urine, lymph fluids, and various external secretions of the respiratory, intestinal and genitorurinary tracts, tears, saliva, milk, white blood cells, myelomas and the like; biological fluids such as cell culture supernatants; fixed tissue specimens; and fixed cell specimens.

"Purified product" refers to a preparation of the product which has been isolated from the cellular constituents with which the product is normally associated, and from other types of cells which may be present in the sample of interest.

"PNA" denotes a "peptide nucleic acid analog" which may be utilized in a procedure such as an assay described herein to determine the presence of a target. "MA" denotes a "morpholino analog" which may be utilized in a procedure such as an assay described herein to determine the presence of a target. See, for example, U.S. Pat. No. 5,378,841, which is incorporated herein by reference. PNAs are neutrally charged moieties which can be directed against RNA targets or DNA. PNA probes used in assays in place of, for example, the DNA probes of the present invention, offer advantages not achievable when DNA probes are used. These advantages include manufacturability, large scale labeling, reproducibility, stability, insensitivity to changes in ionic strength and resistance to enzymatic degradation which is present in methods utilizing DNA or RNA. These PNAs can be labeled with such signal generating compounds as fluorescein, radionucleotides, chemiluminescent compounds, and the like. PNAs or other nucleic acid analogs such as MAs thus can be used in assay methods in place of DNA or RNA. Although assays are described herein utilizing DNA probes, it is within the scope of the routineer that PNAs or MAs can be substituted for RNA or DNA with appropriate changes if and as needed in assay reagents.

"Analyte," as used herein, is the substance to be detected which may be present in the test sample. The analyte can be any substance for which there exists a naturally occurring specific binding member (such as, an antibody), or for which a specific binding member can be prepared. Thus, an analyte is a substance that can bind to one or more specific binding members in an assay. "Analyte" also includes any antigenic substances, haptens, antibodies, and combinations thereof. As a member of a specific binding pair, the analyte can be detected by means of naturally occurring specific binding partners (pairs) such as the use of intrinsic factor protein as a member of a specific binding pair for the determination of Vitamin B12, the use of folate-binding protein to determine folic acid, or the use of a lectin as a member of a specific binding pair for the determination of a carbohydrate. The analyte can include a protein, a peptide, an amino acid, a nucleotide target, and the like.

An "Expressed Sequence Tag" or "EST" refers to the partial sequence of a cDNA insert which has been made by reverse transcription of mRNA extracted from a tissue, followed by insertion into a vector.

A "transcript image" refers to a table or list giving the quantitative distribution of ESTs in a library and represents the genes active in the tissue from which the library was made.

The present invention provides assays which utilize specific binding members. A "specific binding member," as used herein, is a member of a specific binding pair. That is, two different molecules where one of the molecules through chemical or physical means specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, antibodies and antibody fragments, both monoclonal and polyclonal, and complexes thereof, including those formed by recombinant DNA molecules.

The term "hapten," as used herein, refers to a partial antigen or non-protein binding member which is capable of binding to an antibody, but which is not capable of eliciting antibody formation unless coupled to a carrier protein.

A "capture reagent," as used herein, refers to an unlabeled specific binding member which is specific either for the analyte as in a sandwich assay, for the indicator reagent or analyte as in a competitive assay, or for an ancillary specific binding member, which itself is specific for the analyte, as in an indirect assay. The capture reagent can be directly or indirectly bound to a solid phase material before the performance of the assay or during the performance of the assay, thereby enabling the separation of immobilized complexes from the test sample.

The "indicator reagent" comprises a "signal-generating compound" ("label") which is capable of generating and generates a measurable signal detectable by external means, conjugated ("attached") to a specific binding member. The indicator reagent can be a member of any specific binding pair including hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme, and the like. An immunoreactive specific binding member can be an antibody, an antigen, or an antibody/antigen complex that is capable of binding either to polypeptide of interest as in a sandwich assay, to the capture reagent as in a competitive assay, or to the ancillary specific binding member as in an indirect assay. When describing probes and probe assays, the term "reporter molecule" may be used. A reporter molecule comprises a signal generating compound as described hereinabove conjugated to a specific binding member of a specific binding pair, such as carbazol or adamantane.

The various "signal-generating compounds" (labels) contemplated include chromogens, catalysts such as enzymes, luminescent compounds such as fluorescein and rhodamine, chemiluminescent compounds such as dioxetanes, acridiniums, phenanthridiniums and luminol, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction with one or more additional substances.

"Solid phases" ("solid supports") are known to those in the art and include the walls of wells of a reaction tray, test tubes, polystyrene beads, magnetic beads, nitrocellulose strips, membranes, microparticles such as latex particles, sheep (or other animal) red blood cells, and Duracytes® (red blood cells "fixed" by pyruvic aldehyde and formaldehyde, available from Abbott Laboratories, Abbott Park, Ill.) and others. The "solid phase" is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and Duracytes® are all suitable examples. Suitable methods for immobilizing peptides on solid phases include ionic, hydrophobic, covalent interactions and the like. A "solid phase", as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, Duracytes® and other configurations known to those of ordinary skill in the art.

It is contemplated and within the scope of the present invention that the solid phase also can comprise any suitable porous material with sufficient porosity to allow access by detection antibodies and a suitable surface affinity to bind antigens. Microporous structure generally are preferred, but materials with gel structure in the hydrated state may be used as well. Such useful solid supports include but are not limited to nitrocellulose and nylon. It is contemplated that such porous solid supports described herein preferably are in the form of sheets of thickness from about 0.01 to 0.5 mm, preferably about 0.1 mm. The pore size may vary within wide limits, and preferably is from about 0.025 to 15 microns, especially from about 0.15 to 15 microns. The surface of such supports may be activated by chemical processes which cause covalent linkage of the antigen or antibody to the support. The irreversible binding of the antigen or antibody is obtained, however, in general, by adsorption on the porous material by poorly understood hydrophobic forces. Other suitable solid supports are known in the art.

Reagents

The present invention provides reagents such as polynucleotide sequences derived from a human endosulfine gene, polypeptides encoded therein, and antibodies produced from these polypeptides. The present invention also provides reagents such as oligonucleotide fragments derived from the disclosed polynucleotides and nucleic acid sequences complementary to the these polynucleotides. For example, selected endosulfine-derived polynucleotides can be used in the methods described herein for the detection of normal or altered gene expression. Such methods may employ the endosulfine-derived polynucleotides disclosed herein or oligonucleotides, fragments or derivatives thereof, or nucleic acid sequences complementary to these polynucleotides. Furthermore, the polynucleotides disclosed herein, their complementary sequences or fragments of either can be used in assays to detect, amplify or quantify genes, cDNAs or mRNAs encoding human endosulfine. They also can be used to identify an entire or partial coding region which encodes for a endosulfine polypeptide. They further can be provided in individual containers in the form of a kit for assays, or provided as individual compositions. If provided in a kit for assays, other suitable reagents such as buffers, conjugates and the like may be included.

The polynucleotide(s) may be in the form of mRNA or DNA. Polynucleotides in the form of DNA, cDNA, genomic DNA, and synthetic DNA are within the scope of the present invention. The DNA may be double-stranded or single-stranded, and if single stranded may be the coding (sense) strand or non-coding (anti-sense) strand. The coding sequence which encodes the polypeptide may be identical to the coding sequence provided herein or may be a different coding sequence which coding sequence, as a result of the redundancy or degeneracy of the genetic code, encodes the same polypeptide as the DNA provided herein.

This polynucleotide may include only the coding sequence for the polypeptide, or the coding sequence for the polypeptide and additional coding sequence such as a leader or secretory sequence or a proprotein sequence, or the coding sequence for the polypeptide (and optionally additional coding sequence) and non-coding sequence, such as a non-coding sequence 5' and/or 3' of the coding sequence for the polypeptide.

In addition, the invention includes variant polynucleotides containing modifications such as polynucleotide deletions, substitutions or additions; and any polypeptide modification resulting from the variant polynucleotide sequence. A polynucleotide of the present invention also may have a coding sequence which is a naturally occurring allelic variant of the coding sequence provided herein.

In addition, the coding sequence for the polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the form of the polypeptide. The polynucleotides may also encode for a proprotein which is the protein plus additional 5' amino acid residues. A protein having a prosequence is a proprotein and may in some cases be an inactive form of the protein. Once the prosequence is cleaved an active protein remains. Thus, the polynucleotide of the present invention may encode for a protein, or for a protein having a prosequence or for a protein having both a presequence (leader sequence) and a prosequence.

The polynucleotides of the present invention may also have the coding sequence fused in frame to a marker sequence which allows for purification of the polypeptide of the present invention. The marker sequence may be a hexa-histidine tag supplied by a pProEx1 (Life Technologies, Gaithersburg, Md.) vector to provide for purification of the polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein. See, for example, I. Wilson, et al., *Cell* 37:767 (1984).

It is contemplated that polynucleotides which encode a human endosulfine will be considered to hybridize to the sequences provided herein if there is at least 90%, and more preferably at least 95%, identity between the polynucleotide and the sequence.

The present invention also provides an antibody produced by using a purified endosulfine gene polypeptide of which at least a portion of the polypeptide is encoded by an endosufine gene polynucleotide selected from the polynucleotides provided herein. These antibodies may be used in the methods provided herein for the detection of endosulfine polypeptides in test samples. The antibody also may be used for therapeutic purposes, for example, in neutralizing the activity of an endosulfine polypeptide in conditions associated with altered or abnormal expression of endosulfine.

The present invention further provides endosulfine polypeptides which have the deduced amino acid sequences as provided herein, as well as fragments, analogs and derivatives of such polypeptides. The polypeptides of the present invention may be a recombinant polypeptides, natural purified polypeptides or a synthetic polypeptides. The fragments, derivatives or analogs of the endosulfine polypeptides may be those in which one or more of the amino acid residues is substituted with a conserved or non-conserved amino acid residue (preferably a conserved amino acid residue) and such substituted amino acid residue may or may not be one encoded by the genetic code; or it may be one in which one or more of the amino acid residues includes a substituent group; or it may be one in which the polypeptide is fused with another compound, such as a compound to increase the half-life of the polypeptide (for example, polyethylene glycol); or it may be one in which the additional amino acids are fused to the polypeptide, such as a leader or secretory sequence or a sequence which is employed for purification of the polypeptide or a proprotein sequence. Such fragments, derivatives and analogs are within the scope of the present invention. The polypeptides and polynucleotides of the present invention are preferably provided in an isolated form, and preferably purified.

Thus, a polypeptide of the present invention may have an amino acid sequence that is identical to that of the naturally occurring polypeptide or that is different by minor variations due to one or more amino acid substitutions. The variation may be a "conservative change" typically in the range of about 1 to 5 amino acids, wherein the substituted amino acid has similar structural or chemical properties, eg, replacement of leucine with isoleucine or threonine with serine. In contrast, variations may include nonconservative changes, eg, replacement of a glycine with a tryptophan. Similar minor variations may also include amino acid deletions or insertions, or both. Guidance in determining which and how many amino acid residues may be substituted, inserted or deleted without changing biological or immunological activity may be found using computer programs well known in the art, for example, DNASTAR software (DNASTAR Inc., Madison, Wis.).

The endosulfine polypeptides may be naturally purified products expressed from a high expressing cell line, or produced by recombinant techniques from a prokaryotic or eukaryotic host (for example, by bacterial, yeast, higher plant, insect and mammalian cells in culture) as described above. Depending upon the host employed in a recombinant production procedure, the polypeptides of the present invention may be glycosylated with mammalian or other eukaryotic carbohydrates or may be non-glycosylated. The polypeptides of the invention may also include an initial methionine amino acid residue. Alternatively, the polypeptides of the invention can be synthetically produced by conventional peptide synthesizers or produced by cell-free translation systems using RNAs derived from the DNA constructs of the present invention.

Probe Assays

The sequences provided herein may be used to produce probes which can be used in assays for the detection of nucleic acids in test samples. For example, such probes can be used in Fluorescent In Situ Hybridization (FISH) technology to perform chromosomal analysis, and used to identify endosulfine structural alterations in the chromosomes, such as deletions or translocations that are visible from chromosome spreads or detectable using PCR-generated and/or allele specific oligonulcleotides probes, allele specific amplification or by direct sequencing. Probes also can be labeled with radioisotopes, directly- or indirectly-detectable haptens, or fluorescent molecules, and utilized for in situ hybridization studies to evaluate the mRNA expression of the gene comprising the polynucleotide in fixed tissue specimens or cells.

The probes may be designed from conserved nucleotide regions of the polynucleotides of interest or from non-conserved nucleotide regions of the polynucleotide of interest. The design of such probes for optimization in assays is within the skill of the routineer. Generally, nucleic acid probes are developed from non-conserved or unique regions when maximum specificity is desired, and nucleic acid probes are developed from conserved regions when assaying for nucleotide regions that are closely related to, for example, different members of a multigene family or in related species like mouse and man.

The polymerase chain reaction (PCR) is a technique for amplifying a desired nucleic acid sequence (target) contained in a nucleic acid or mixture thereof. In PCR, a pair of primers are employed in excess to hybridize at the outside ends of complementary strands of the target nucleic acid. The primers are each extended by a polymerase using the target nucleic acid as a template. The extension products become target sequences themselves, following dissociation from the original target strand. New primers then hybridize to the target sequences and are extended by a polymerase, and the cycle is repeated to geometrically increase the number of target sequence molecules. PCR is disclosed in U.S. Pat. Nos. 4,683,195 and 4,683,202, which are incorporated herein by reference.

The Ligase Chain Reaction (LCR) is an alternate method for nucleic acid amplification. In LCR, probe pairs are used which include two primary (first and second) and two secondary (third and fourth) probes, all of which are employed in molar excess to a target. The first probe hybridizes to a first segment of the target strand and the second probe hybridizes to a second segment of the target strand, the first and second segments being contiguous so that the primary probes abut one another in 5' phosphate-3'hydroxyl relationship, and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. Of course, if the target is initially double stranded, the secondary probes also will hybridize to the target complement in the first instance. Once the ligated strand of primary probes is separated from the target strand, it will hybridize with the third and fourth probes which can be ligated to form a complementary, secondary ligated product. It is important to realize that the ligated products are functionally equivalent to either the target or its complement. By repeated cycles of hybridization and ligation, amplification of the target sequence is achieved. This technique is described more completely in EP-A-320 308 to K. Backman published Jun. 16, 1989 and EP-A-439 182 to K. Backman et al., published Jul. 31, 1991, both of which are incorporated herein by reference.

For amplification of mRNAs, it is within the scope of the present invention to reverse transcribe mRNA into cDNA followed by polymerase chain reaction (RT-PCR); or, to use a single enzyme for both steps as described in U.S. Pat. No. 5,322,770, which is incorporated herein by reference; or reverse transcribe mRNA into cDNA followed by asymmetric gap ligase chain reaction (RT-AGLCR) as described by R. L. Marshall, et al., *PCR Methods and Applications* 4: 80–84 (1994), which also is incorporated herein by reference.

Other known amplification methods which can be utilized herein include but are not limited to the so-called "NASBA" or "3SR" technique described in *PNAS USA* 87:1874–1878 (1990) and also described in *Nature* 350 (No. 6313):91–92 (1991); Q-beta amplification as described in published European Patent Application (EPA) No. 4544610; strand displacement amplification (as described in G. T. Walker et al., *Clin. Chem.* 42:9–13 (1996)) and European Patent Application No. 684315; and target mediated amplification, as described by PCT Publication WO 9322461.

In one embodiment, the present invention generally comprises the steps of contacting a test sample suspected of containing a target polynucleotide sequence with amplification reaction reagents comprising an amplification primer, and a detection probe that can hybridize with an internal region of the amplicon sequences. Probes and primers employed according to the method herein provided are labeled with capture and detection labels wherein probes are labeled with one type of label and primers are labeled with the other type of label. Additionally, the primers and probes are selected such that the probe sequence has a lower melt temperature than the primer sequences. The amplification reagents, detection reagents and test sample are placed under amplification conditions whereby, in the presence of target sequence, copies of the target sequence (an amplicon) are produced. In the usual case, the amplicon is double stranded because primers are provided to amplify a target sequence and its complementary strand. The double stranded amplicon then is thermally denatured to produce single stranded amplicon members. Upon formation of the single stranded amplicon members, the mixture is cooled to allow the formation of complexes between the probes and single stranded amplicon members.

As the single stranded amplicon sequences and probe sequences are cooled, the probe sequences preferentially bind the single stranded amplicon members. This finding is counterintuitive given that the probe sequences are generally selected to be shorter than the primer sequences and therefore have a lower melt temperature than the primers. Accordingly, the melt temperature of the amplicon produced by the primers should also have a higher melt temperature than the probes. Thus, as the mixture is cooled, the re-formation of the double stranded amplicon is expected. As previously stated, however, this is not the case. Probes have been found to preferentially bind the single stranded amplicon members. Moreover, this preference of probe/single stranded amplicon binding exists even when the primer sequences are added in excess of the probes.

After the probe/single stranded amplicon member hybrids are formed, they are detected. Standard heterogeneous assay formats are suitable for detecting the hybrids using the detection labels and capture labels present on the primers and probes. The hybrids can be bound to a solid phase reagent by virtue of the capture label and detected by virtue of the detection label. In cases where the detection label is directly detectable, the presence of the hybrids on the solid phase can be detected by causing the label to produce a detectable signal, if necessary, and detecting the signal. In cases where the label is not directly detectable, the captured hybrids can be contacted with a conjugate, which generally comprises a binding member attached to a directly detectable label. The conjugate becomes bound to the complexes and the conjugates presence on the complexes can be detected with the directly detectable label. Thus, the presence of the hybrids on the solid phase reagent can be determined. Those skilled in the art will recognize that wash steps may be employed to wash away unhybridized amplicon or probe as well as unbound conjugate.

A test sample is typically anything suspected of containing a target sequence. Test samples can be prepared using methodologies well known in the art such as by obtaining a specimen from an individual and, if necessary, disrupting any cells contained therein to release target nucleic acids. Although the target sequence is described as single stranded, it also is contemplated to include the case where the target sequence is actually double stranded but is merely separated from its complement prior to hybridization with the amplification primer sequences. In the case where PCR is employed in this method, the ends of the target sequences are usually known. In cases where LCR or a modification thereof is employed in the preferred method, the entire target sequence is usually known. Typically, the target sequence is a nucleic acid sequence such as, for example, RNA or DNA.

The method provided herein can be used in well known amplification reactions that include thermal cycle reaction mixtures, particularly in PCR and GLCR. Amplification reactions typically employ primers to repeatedly generate copies of a target nucleic acid sequence, which target sequence is usually a small region of a much larger nucleic acid sequence. Primers are themselves nucleic acid sequences that are complementary to regions of a target sequence. Under amplification conditions, these primers hybridize or bind to the complementary regions of the target sequence. Copies of the target sequence typically are generated by the process of primer extension and/or ligation which utilizes enzymes with polymerase or ligase activity, separately or in combination, to add nucleotides to the hybridized primers and/or ligate adjacent probe pairs. The nucleotides that are added to the primers or probes, as monomers or preformed oligomers, are also complementary to the target sequence. Once the primers or probes have been sufficiently extended and/or ligated they are separated from the target sequence, for example, by heating the reaction mixture to a "melt temperature" which is one in which complementary nucleic acid strands dissociate. Thus, a sequence complementary to the target sequence is formed.

A new amplification cycle then can take place to further amplify the number of target sequences by separating any double stranded sequences, allowing primers or probes to hybridize to their respective targets, extending and/or ligating the hybridized primers or probes and re-separating. The complementary sequences that are generated by amplification cycles can serve as templates for primer extension or filling the gap of two probes to further amplify the number of target sequences. Typically, a reaction mixture is cycled between 20 and 100 times, more typically, a reaction mixture is cycled between 25 and 50 times. The numbers of cycles can be determined by the routineer. In this manner, multiple copies of the target sequence and its complementary sequence are produced. Thus, primers initiate amplification of the target sequence when it is present under amplification conditions.

Generally, two primers which are complementary to a portion of a target strand and its complement are employed in PCR. For LCR, four probes, two of which are complementary to a target sequence and two of which are similarly complementary to the targets complement, are generally employed. In addition to the primer sets and enzymes previously mentioned, a nucleic acid amplification reaction mixture may also comprise other reagents which are well known and include but are not limited to: enzyme cofactors such as manganese; magnesium; salts; nicotinamide adenine dinucleotide (NAD); and deoxynucleotide triphosphates (dNTPs) such as for example deoxyadenine triphosphate, deoxyguanine triphosphate, deoxycytosine triphosphate and deoxythymine triphosphate.

While the amplification primers initiate amplification of the target sequence, in some cases, the detection (or hybridization) probe is not involved in amplification. Detection probes are generally nucleic acid sequences or uncharged nucleic acid analogs such as, for example, peptide nucleic acids which are disclosed in International Patent Application WO 92/20702; morpholino analogs which are described in U.S. Pat. Nos. 5,185,444, 5,034,506, and 5,142,047; and the like. Depending upon the type of label carried by the probe, the probe is employed to capture or detect the amplicon generated by the amplification reaction. The probe is not involved in amplification of the target sequence and therefore may have to be rendered "non-extendable" in that additional dNTPs cannot be added to the probe. In and of themselves analogs usually are non-extendable and nucleic acid probes can be rendered non-extendable by modifying the 3' end of the probe such that the hydroxyl group is no longer capable of participating in elongation. For example, the 3' end of the probe can be functionalized with the capture or detection label to thereby consume or otherwise block the hydroxyl group. Alternatively, the 3' hydroxyl group simply can be cleaved, replaced or modified. U.S. patent application Ser. No. 07/049,061 filed Apr. 19, 1993 and incorporated herein by reference describes modifications which can be used to render a probe non-extendable.

Accordingly, in this circumstance, the ratio of primers to probes is not important. Thus, either the probes or primers can be added to the reaction mixture in excess whereby the concentration of one would be greater than the concentration of the other. Alternatively, primers and probes can be employed in equivalent concentrations. Preferably, however, the primers are added to the reaction mixture in excess of the probes. Thus, when a probe is not involved in the amplification process, primer to probe ratios of, for example, 5:1 and 20:1 are preferred.

While the length of the primers and probes can vary, the probe sequences are selected such that they have a lower melt temperature than the primer sequences. Hence, the primer sequences are generally longer than the probe sequences. Typically, the primer sequences are in the range of between 20 and 50 nucleotides long, more typically in the range of between 20 and 30 nucleotides long. The typical probe is in the range of between 10 and 25 nucleotides long.

Alternatively, a probe may be involved in the amplifying a target sequence, via a process known as "nested PCR". In nested PCR, the probe has characteristics which are similar to those of the first and second primers normally used for amplification (such as length, melting temperature etc.) and as such, may itself serve as a primer in an amplification reaction. Generally in nested PCR, a first pair of primers ($P_1$ and $P_2$) are employed to form primary extension products. One of the primary primers (for example, $P_1$) may optionally be a capture primer (i.e. linked to a member of a first reactive pair), whereas the other primary primer ($P_2$) is not. A secondary extension product is then formed using the $P_1$ primer and a probe ($P_{2'}$) which may also have a capture type label (such as a member of a second reactive pair) or a detection label at its 5' end. The probe is complimentary to and hybridizes at a site on the template near or adjacent (but not overlapping) the site where the 3' terminus of $P_2$ would hybridize if it was still in solution. Thus, a labeled primer/probe set generates a secondary product which is shorter than the primary extension product. Furthermore, the secondary product may be detected either on the basis of its. size or via its labeled ends (by detection methodologies well known to those of ordinary skill in the art). In this process, probe and primers are generally employed in equivalent concentrations.

Various methods for synthesizing primers and probes are well known in the art. Similarly, methods for attaching labels to primers or probes are also well known in the art. For example, it is a matter of routine to synthesize desired nucleic acid primers or probes using conventional nucleotide phosphoramidite chemistry and instruments available from Applied Biosystems, Inc., (Foster City, Calif.), Dupont (Wilmington, Del.), or Milligen (Bedford Mass.). Many methods have been described for labeling oligonucleotides such as the primers or probes of the present invention. Enzo Biochemical (New York, N.Y.) and Clontech (Palo Alto, Calif.) both have described and commercialized probe labeling techniques. For example, a primary amine can be attached to a 3' oligo terminus using 3'-Amine-ON CPG™ (Clontech, Palo Alto, Calif.). Similarly, a primary amine can be attached to a 5' oligo terminus using Aminomodifier II® (Clontech). The amines can be reacted to various haptens using conventional activation and linking chemistries. In addition, copending applications U.S. Ser. No. 625,566, filed Dec. 11, 1990 and Ser. No. 630,908, filed Dec. 20, 1990, which are each incorporated herein by reference, teach methods for labeling probes at their 5' and 3' termini, respectively. Publications WO92/10505, published Jun. 25, 1992 and WO 92/11388 published Jul. 9, 1992 teach methods for labeling probes at their 5' and 3' ends, respectively. According to one known method for labeling an oligonucleotide, a label-phosphoramidite reagent is prepared and used to add the label to the oligonucleotide during its synthesis. See, for example, N. T. Thuong et al., Tet. Letters 29(46):5905–5908 (1988); or J. S. Cohen et al., published U.S. patent application Ser. No. 07/246,688 (NTIS ORDER No. PAT-APPL-7-246,688) (1989). Preferably, probes are labeled at their 3' and 5' ends.

Capture labels are carried by the primers or probes and can be a specific binding member which forms a binding pair with the solid phase reagent's specific binding member. It will be understood, of course that the primer or probe itself may serve as the capture label. For example, in the case where a solid phase reagent's binding member is a nucleic acid sequence, it may be selected such that it binds a complementary portion of the primer or probe to thereby immobilize the primer or probe to the solid phase. In cases where the probe itself serves as the binding member, those skilled in the art will recognize that the probe will contain a sequence or "tail" that is not complementary to the single stranded amplicon members. In the case where the primer itself serves as the capture label, at least a portion of the primer will be free to hybridize with a nucleic acid on a solid phase because the probe is selected such that it is not fully complementary to the primer sequence.

Another method provided by the present invention comprises contacting a test sample with a plurality of polynucleotides wherein at least one polynucleotide is provided herein, hybridizing the test sample with the plurality of polynucleotides and detecting the hybridization complexes. The hybridization complexes are identified and quantitated to compile a profile which is indicative of endosulfine expression. Expressed RNA sequences may further be detected by reverse transcription and amplification of the DNA product by procedures well-known in the art, including polymerase chain reaction (PCR).

Drug Screening and Gene Therapy.

The present invention also encompasses the use of gene therapy methods for the introduction of anti-sense endosulfine gene derived molecules such as polynucleotides or oligonucleotides of the present invention into patients with conditions associated with abnormal expression of polynucleotides related to endosulfine. These molecules, including antisense RNA and DNA fragments and ribozymes, are designed to inhibit the translation of an endosulfine mRNA, and may be used therapeutically in the treatment of conditions associated with altered or abnormal expression of an endosulfine polynucleotide.

Alternatively, the oligonucleotides described above can be delivered to cells by procedures in the art such that the anti-sense RNA or DNA may be expressed in vivo to inhibit production of an endosulfine polypeptide in the manner described above. Antisense constructs to endosulfine polynucleotides, therefore, reverse the action of endosulfine transcripts.

The present invention also provides a method of screening a plurality of compounds for specific binding to a human endosulfine polypeptide, or any fragment thereof, to identify at least one compound which specifically binds a human endosulfine polypeptide. Such a method comprises the steps of providing at least one compound; combining the endosulfine polypeptide with each compound under suitable conditions for a time sufficient to allow binding; and detecting an endosulfine polypeptide binding to each compound. Such a method permits the identification of endosulfine binding compounds which modulate (i.e. inhibit or activate) the activity of endosulfine.

Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the polypeptide of the present invention, is used to design an antisense RNA oligonucleotide of from 10 to 40 base pairs in length. A DNA oligonucleotide is designed to be complementary to a region of the gene involved in transcription, thereby preventing transcription and the production of endosulfine derived polypeptide. For triple helix, see, for example, Lee et al., Nucl. Acids Res. 6:3073 (1979); Cooney et al., Science 241:456 (1988); and Dervan et al., Science 251:1360 (1991) The antisense RNA oligonucleotide hybridizes to the mRNA in vivo and either blocks translation of an mRNA molecule into the endosulfine polypeptide or alters the transport or stability of the mRNA. For antisense, see, for example, Okano, J. Neurochem. 56:560 (1991); and "Oligodeoxynucleotides as Antisense Inhibitors of Gene Expression", CRC Press, Boca Raton, Fla. (1988). Antisense oligonucleotides act with greater efficacy when modified to contain artificial internucleotide linkages which render the molecule resistant to nucleolytic cleavage. Such artificial internucleotide linkages include but are not limited to methylphosphonate, phosphorothiolate and phosphoroamydate internucleotide linkages.

The polypeptide or peptide fragment employed in such a test may either be free in solution, affixed to a solid support, borne on a cell surface or located intracellularly. One method of drug screening utilizes eukaryotic or prokaryotic host cells which are stably transformed with recombinant nucleic acids which can express the polypeptide or peptide fragment. Drugs may be screened against such transformed cells in competitive binding assays. For example, the formation of complexes between a polypeptide and the agent being tested can be measured in either viable or fixed cells.

The present invention thus provides methods of screening for drugs or any other agent which can be used to treat diseases associated with ATP sensitive potassium channels. These methods comprise contacting the drug with a polypeptide or fragment thereof and assaying for either the presence of a complex between the agent and the polypeptide, or for the presence of a complex between the polypeptide and the cell. In competitive binding assays, the polypeptide typically is labeled. After suitable incubation, free (or uncomplexed) polypeptide or fragment thereof is separated from that present in bound form, and the amount of free or uncomplexed label is a measure of the ability of the particular drug to bind to polypeptide or to interfere with the polypeptide/cell complex.

The present invention also encompasses the use of competitive drug screening assays in which neutralizing antibodies capable of binding polypeptide specifically compete with a test drug for binding to the polypeptide or fragment thereof. In this manner, the antibodies can be used to detect the presence of any polypeptide in the test sample which shares one or more antigenic determinants with a polypeptide provided herein.

Another technique for drug screening provides high throughput screening for compounds having suitable binding affinity to at least one polypeptide disclosed herein. Briefly, large numbers of different small peptide test compounds are synthesized on a solid phasee, such as plastic pins or some other surface. The peptide test compounds are reacted with polypeptide and washed. Polypeptide thus bound to the solid phase is detected by methods well-known in the art. Purified polypeptide can also be coated directly onto plates for use in the drug screening techniques described herein. In addition, non-neutralizing antibodies can be used to capture the polypeptide and immobilize it on the solid support. See, for example, EP 84/03564, published on Sep. 13, 1984, which is incorporated herein by reference The goal of rational drug design is to produce structural analogs of biologically active polypeptides of interest or of the small molecules including agonists, antagonists, or inhibitors with which they interact. Such structural analogs can be used to fashion drugs which are more active or stable forms of the polypeptide or which enhance or interfere with the function of a polypeptide in vivo. J. Hodgson, *Bio/Technology* 9:19–21 (1991), incorporated herein by reference.

For example, in one approach, the three-dimensional structure of a polypeptide, or of a polypeptide-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide may be gained by modeling based on the structure of homologous proteins. In both cases, relevant structural information is used to design analogous polypeptide-like molecules or to identify efficient inhibitors.

Useful examples of rational drug design may include molecules which have improved activity or stability as shown by S. Braxton et al., *Biochemistry* 31:7796–7801 (1992), or which act as inhibitors, agonists, or antagonists of native peptides as shown by S. B. P. Athauda et al., *J Biochem.* (*Tokyo*) 113 (6):742–746 (1993), incorporated herein by reference.

It also is possible to isolate a target-specific antibody, selected by an assay as described hereinabove, and then to determine its crystal structure. In principle this approach yields a pharmacophore upon which subsequent drug design can be based. It further is possible to bypass protein crystallography altogether by generating anti-idiotypic antibodies ("anti-ids") to a functional, pharmacologically active antibody. As a mirror image of a mirror image, the binding site of the anti-id is an analog of the original receptor. The anti-id then could be used to identify and isolate peptides from banks of chemically or biologically produced peptides. The isolated peptides then can act as the pharmacophore (that is, a prototype pharmaceutical drug).

A sufficient amount of a recombinant polypeptide of the present invention may be made available to perform analytical studies such as X-ray crystallography. In addition, knowledge of the polypeptide amino acid sequence which are derivable from the nucleic acid sequence provided herein will provide guidance to those employing computer modeling techniques in place of or in addition to x-ray crystallography.

Antibodies specific to a human endosulfine polypeptide may further be used to inhibit the biological action of the polypeptide by binding to the polypeptide. In this manner, the antibodies may be used in therapy, for example, to treat disorders involving ATP-sensitive potassium channels.

Further, such antibodies can detect the presence or absence of a human endosulfine polypeptide and, therefore, are useful as diagnostic markers for the diagnosis of disorders involving ATP-sensitive potassium channels. The present invention also is directed to antagonists and inhibitors of the polypeptides of the present invention. The antagonists and inhibitors are those which inhibit or eliminate the function of the polypeptide. Thus, for example, an antagonist may bind to a polypeptide of the present invention and inhibit or eliminate its function.

The antagonists and inhibitors may be employed as a composition with a pharmaceutically acceptable carrier, including but not limited to saline, buffered saline, dextrose, water, glycerol, ethanol and combinations thereof.

Recombinant Technology.

The present invention provides vectors which include polynucleotides of the present invention, host cells which are genetically engineered with vectors of the present invention and the production of polypeptides of the present invention by recombinant techniques. Such methods comprise culturing the host cells under conditions suitable for the expression of a human endosulfine polynucleotide and recovering the polypeptide produced therefrom from the cell culture.

a. Host Cells

In one embodiment, the present invention provides host cells containing a recombinant construct as described below. The host cell can be a higher eukaryotic cell, such as a mammalian cell, or a lower eukaryotic cell, such as a yeast cell, or a prokaryotic cell, such as a bacterial cell. Representative examples of appropriate hosts include bacterial cells, such as *E. coli, Bacillus subtilis, Salmonella typhimurium*; and various species within the genera *Pseudomonas, Streptomyces,* and *Staphylococcus*, although others may also be employed as a routine matter of choice; fungal cells, such as yeast; insect cells such as *Drosophila* and Sf9; animal cells such as CHO, COS or Bowes melanoma; plant cells, etc. The selection of an appropriate host is deemed to be within the scope of those skilled in the art from the teachings provided herein.

Host cells are genetically engineered (transduced or transformed or transfected) with the vectors of this invention which may be a cloning vector or an expression vector. The engineered host cells can be cultured in conventional nutrient media modified as appropriate for activating promoters, selecting transformants or amplifying an endosulfine gene. The culture conditions, such as temperature, pH and the like, are those previously used with the host cell selected for expression, and will be apparent to the ordinarily skilled artisan.

b. Vectors and Expression Systems

The present invention also includes recombinant constructs comprising one or more of the sequences as broadly described above. The constructs comprise a vector, such as a plasmid or viral vector, into which a sequence of the invention has been inserted, in a forward or reverse orientation. Such vectors include chromosomal, nonchromosomal and synthetic DNA sequences, e.g., derivatives of SV40; bacterial plasmids; phage DNA; yeast plasmids; vectors derived from combinations of plasmids and phage DNA, and viral DNA such as vaccinia, adenovirus, fowl pox virus, and pseudorabies. In a preferred embodiment, a construct comprises an expression vector (as described below). Large numbers of suitable plasmids and vectors are known to those of skill in the art, and are commercially available. The following vectors are provided by way of example: (a) Bacterial: pBR322 (ATCC 37017); pGEM1 (Promega Biotec, Madison, Wis.), pUC, pSPORT1 and pProEx1 (Life Technologies, Gaithersburg, Md.); pQE70, pQE60, pQE-9 (Qiagen); pBs, phagescript, psiX174, pBluescript SK, pBsKS, pNH8a, pNH16a, pNH18a, pNH46a (Stratagene); pTrc99A, pKK223-3, pKK233-3, pDR540, pRIT5, and pGEX4T (Pharmacia Fine Chemicals, Uppsala, Sweden); and (b) Eukaryotic: pWLneo, pSV2cat, pOG44, pXT1, pSG (Stratagene); pSVK3, pBPV, pMSG, pSVL (Pharmacia); pcDNA3.1 (Invitrogen). Other appropriate cloning and expression vectors for use with prokaryotic and eukaryotic hosts are described by Sambrook et al., *Molecular Cloning: A Laboratory Manual,* Second Edition, (Cold Spring Harbor, N.Y., 1989), which is hereby incorporated by reference. Generally however, any plasmid or vector may be used as long as it is replicable and viable in a host.

In a preferred embodiment, the construct is an expression vector which also comprises regulatory sequences operably linked to the sequence of interest, to direct mRNA synthesis and polypeptide production. Regulatory sequences known to operate in prokaryotic and/or eukaryotic cells include inducible and non-inducible promoters for regulating mRNA transcription, ribosome binding sites for translation initiation, stop codons for translation termination and transcription terminators and/or polyadenylation signals. In addition, an expression vector may include appropriate sequences for amplifying expression (such as a dihydrofolate reductase gene).

Promoter regions may be selected from any desired gene but preferably from one which is highly expressed. Particular named bacterial promoters include lacZ, gpt, lambda P sub R, P sub L and trp. Eukaryotic promoters include cytomegalovirus (CMV) immediate early, herpes simplex virus (HSV) thymidine kinase, early and late SV40, LTRs from retroviruses, mouse metallothionein-I, prion protein and neuronal specific enolase (NSE). Selection of the appropriate promoter is well within the level of ordinary skill in the art. In addition, a recombinant expression vector will include an origin of replication and selectable marker (such as a gene conferring resistance to an antibiotic (eg. neomycin, chloramphenicol or ampicillin) or a reporter gene (eg. luciferase)) which permit selection of stably transformed or transfected host cells.

In a preferred prokaryotic or yeast expression vector, a heterologous structural sequence (i.e. a polynucleotide of the present invention) is assembled in appropriate phase with translation initiation and termination sequences, and preferably, a leader sequence capable of directing secretion of translated protein into the periplasmic space or extracellular medium. Optionally, the heterologous sequence will encode a fusion protein including an N-terminal identification peptide imparting desired characteristics, e.g., stabilization or simplified purification of expressed recombinant product.

Preferred eukaryotic expression vectors will also comprise an origin of replication, a suitable promoter operably linked to a sequence of interest and also any necessary translation enhancing sequence, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements. Such vectors may also include an enhancer sequence to increase transcription of a gene. Enhancers are cis-acting elements of DNA, usually about from 10 to 300 bp, that act on a promoter to increase its transcription rate. Examples include the SV40 enhancer on the late side of the replication origin (bp 100 to 270), a cytomegalovirus early promoter enhancer, a polyoma enhancer on the late side of the replication origin, and adenovirus enhancers.

i. Vector Construction

The appropriate DNA sequence may be inserted into a vector by a variety of procedures. Generally, site-specific DNA cleavage is performed by treating the DNA with suitable restriction enzymes under conditions which are generally specified by the manufacturer of these commercially available enzymes. Usually, about 1 microgram (µg) of plasmid or DNA sequence is cleaved by 1 unit of enzyme in about 20 microliters (µL) of buffer solution by incubation at 37° C. for 1 to 2 hours. After incubation with the restriction enzyme, protein is removed by phenol/chloroform extraction and the DNA recovered by precipitation with ethanol. The cleaved fragments may be separated using polyacrylamide or agarose gel electrophoresis, according to methods known by the routine practitioner. (See Sambrook et al., supra).

Ligations are performed using standard buffer and temperature conditions and with a ligase (such as T4 DNA ligase) and ATP. Sticky end ligations require less ATP and less ligase than blunt end ligations. When vector fragments are used as part of a ligation mixture, the vector fragment often is treated with bacterial alkaline phosphatase (BAP) or calf intestinal alkaline phosphatase (CIAP) to remove the 5'-phosphate and thus prevent religation of the vector. Alternatively, restriction enzyme digestion of unwanted fragments can be used to prevent ligation. Ligation mixtures are transformed into suitable cloning hosts such as *E. coli* and successful transformants selected by methods including antibiotic resistance, and then screened for the correct construct.

ii. Transformation/Transfection

Transformation or transfection of an appropriate host with a construct of the invention, such that the host produces recombinant polypeptides, may also be performed in a variety of ways. For example, a construct may be introduced into a host cell by calcium chloride transformation, lithium chloride or calcium phosphate transfection, DEAE-Dextran mediated transfection, or electroporation. These and other methods for transforming/transfecting host cells are well known to routine practitioners (see L. Davis et al., "Basic Methods in Molecular Biology", 2nd edition, Appleton and Lang, Paramount Publishing, East Norwalk, Conn. (1994)).

iii. Recovery of Expressed Proteins from Recombinant Host Cells

Following transformation or transfection of a suitable host strain and growth of the host strain to an appropriate cell density, the selected promoter is derepressed by appropriate means (e.g., temperature shift or chemical induction), and cells are cultured for an additional period. Cells are typically harvested by centrifugation, disrupted by physical or chemical means (to release intracellular protein) and the resulting crude extract retained for further purification. Microbial cells employed in expression of proteins can be disrupted by any convenient method, including freeze-thaw cycling, sonication, mechanical disruption, or use of cell lysing agents; such methods are well-known to the ordinary artisan. When the expressed protein has been secreted, it can be purified directly from the supernatant of harvested cells.

Endosulfine polypeptide is recovered and purified from the supernatant or crude extract by known methods including ammonium sulfate or ethanol precipitation, acid extraction, affinity chromatography, anion or cation exchange chromatography, phosphocellulose chromatography, hydrophobic interaction chromatography, hydroxyapatite chromatography or lectin chromatography. It is preferred to have low concentrations (approximately 0.1–5 mM) of calcium ion present during purification (Price, et al., *J. Biol. Chem.* 244:917 (1969)). Protein refolding steps can be used, as necessary, in completing configuration of the protein. Finally, high performance liquid chromatography (HPLC) can be employed for final purification steps.

An alternative method for the production of large amounts of secreted protein involves the transformation of mammalian embryos and the recovery of the recombinant protein from milk produced by transgenic cows, goats, sheep, etc. Polypeptides and closely related molecules may be expressed recombinantly in such a way as to facilitate protein purification. One approach involves expression of a chimeric protein which includes one or more additional polypeptide domains not naturally present on human polypeptides. Such purification-facilitating domains include, but are not limited to, metal-chelating peptides such as histidine-tryptophan domains that allow purification on immobilized metals, protein A domains that allow purification on immobilized immunoglobulin, and the domain utilized in the FLAGS extension/affinity purification system (Immunex Corp, Seattle, Wash.). The inclusion of a cleavable linker sequence such as Factor XA or enterokinase from Invitrogen (San Diego, Calif.) between the polypeptide sequence and the purification domain may be useful for recovering the polypeptide.

Immunoassays.

The polypeptides including their fragments or derivatives or analogs thereof of the present invention, or cells expressing them, can be used in a variety of assays, many of which are described herein, for the detection of antibodies to a human endosulfine. They also can be used as an immunogen to produce antibodies. These antibodies can be, for example, polyclonal or monoclonal antibodies, chimeric, single chain and humanized antibodies, as well as Fab fragments, or the product of an Fab expression library. Various procedures known in the art may be used for the production of such antibodies and fragments.

For example, antibodies generated against a polypeptide corresponding to a sequence of the present invention can be obtained by direct injection of the polypeptide into an animal or by administering the polypeptide to an animal such as a mouse, rabbit, chicken, or goat. A mouse, rabbit or goat is preferred. The antibody so obtained then will bind the polypeptide itself. In this manner, even a sequence encoding only a fragment of the polypeptide can be used to generate antibodies that bind the native polypeptide. Such antibodies can then be used to isolate the polypeptide from test samples such as tissue suspected of containing that polypeptide. For preparation of monoclonal antibodies, any technique which provides antibodies produced by continuous cell line cultures can be used. Examples include the hybridoma technique as described by Kohler and Milstein, *Nature* 256: 495–497 (1975), the trioma technique, the human B-cell hybridoma technique as described by Kozbor et al., *Immun. Today* 4: 72 (1983), and the EBV-hybridoma technique to produce human monoclonal antibodies as described by Cole, et al., in *Monoclonal Antibodies and Cancer Therapy*, Alan R. Liss, Inc, New York, N.Y., pp. 77–96 (1985). Techniques described for the production of single chain antibodies can be adapted to produce single chain antibodies to immunogenic polypeptide products of this invention. See, for example, U.S. Pat. No. 4,946,778, which is incorporated herein by reference.

Various assay formats may utilize the antibodies of the present invention, including "sandwich" immunoassays and probe assays. For example, the monoclonal antibodies or fragment thereof of the present invention can be employed in various assay systems to determine the presence, if any, of an endosulfine derived polypeptide in a test sample. For example, in a first assay format, a polyclonal or monoclonal antibody or fragment thereof, or a combination of these antibodies, which has been coated on a solid phase, is contacted with a test sample, to form a first mixture. This first mixture is incubated for a time and under conditions sufficient to form antigen/antibody complexes. Then, an indicator reagent comprising a monoclonal or a polyclonal antibody or a fragment thereof, or a combination of these antibodies, to which a signal generating compound has been attached, is contacted with the antigen/antibody complexes to form a second mixture. This second mixture then is incubated for a time and under conditions sufficient to form antibody/antigen/antibody complexes. The presence of an endosulfine derived polypeptide antigen present in the test sample and captured on the solid phase, if any, is determined by detecting the measurable signal generated by the signal generating compound. The amount of endosulfine derived polypeptide antigen present in the test sample is proportional to the signal generated.

Or, a polyclonal or monoclonal endosulfine derived polypeptide antibody or fragment thereof, or a combination polypeptide antibodies which is bound to a solid support, the test sample and an indicator reagent comprising a monoclonal or polyclonal antibody or fragments thereof, which specifically binds to an endosulfine derived polypeptide antigen, or a combination of these antibodies to which a signal generating compound is attached, are contacted to form a mixture. This mixture is incubated for a time and under conditions sufficient to form antibody/antigen/antibody complexes. The presence, if any, of an endosulfine derived polypeptide present in the test sample and captured on the solid phase is determined by detecting the measurable signal generated by the signal generating compound. The amount of endosulfine derived polypeptide proteins present in the test sample is proportional to the signal generated.

In another assay format, one or a combination of at least two monoclonal antibodies of the invention can be employed as a competitive probe for the detection of antibodies to an endosulfine derived polypeptide protein. For example, endosufine derived polypeptide proteins such as the recombinant antigens disclosed herein, either alone or in combination, are coated on a solid phase. A test sample suspected of containing antibody to an endosulfine derived polypeptide antigen then is incubated with an indicator reagent comprising a signal generating compound and at least one monoclonal antibody of the invention for a time and under conditions sufficient to form antigen/antibody complexes of either the test sample and indicator reagent bound to the solid phase or the indicator reagent bound to the solid phase. The reduction in binding of the monoclonal antibody to the solid phase can be quantitatively measured.

In yet another detection method, each of the monoclonal or polyclonal antibodies of the present invention can be employed in the detection of endosulfine derived polypeptide antigens in fixed tissue sections, as well as fixed cells by immunohistochemical analysis. Cytochemical analysis wherein these antibodies are labeled directly (with, for example, fluorescein, colloidal gold, horseradish peroxidase, alkaline phosphatase, etc.) or are labeled by using secondary labeled anti-species antibodies (with various labels as exemplified herein) to track the histopathology of disease also are within the scope of the present invention.

In addition, these monoclonal antibodies can be bound to matrices similar to CNBr-activated Sepharose and used for the affinity purification of specific endosulfine derived polypeptide proteins from cell cultures or biological tissues such as to purify recombinant and native endosulfine derived polypeptide antigens and proteins.

The monoclonal antibodies of the invention can also be used for the generation of chimeric antibodies for therapeutic use, or other similar applications.

The monoclonal antibodies or fragments thereof can be provided individually to detect endosulfine derived polypeptide antigens. Combinations of the monoclonal antibodies (and fragments thereof) provided herein also may be used together as components in a mixture or "cocktail" of at least one endosulfine derived polypeptide antibody of the invention with antibodies to other endosulfine derived polypeptide regions, each having different binding specificities. Thus, this cocktail can include the monoclonal antibodies which are directed to different antigenic determinants of endosulfine derived polypeptide proteins.

The polyclonal antibody or fragment thereof which can be used in the assay formats should specifically bind to an endosulfine derived polypeptide region or other endosulfine derived polypeptide protein used in the assay. The polyclonal antibody used is preferably of mammalian origin (such as from human, goat, rabbit or sheep). Most preferably, the polyclonal antibody is rabbit polyclonal anti-endosulfine derived polypeptide antibody. The polyclonal antibodies used in the assays can be used either alone or as a cocktail of polyclonal antibodies.

It is contemplated and within the scope of the present invention that an endosulfine derived polypeptide may be detectable in assays by use of a recombinant antigen as well as by use of a synthetic peptide or purified peptide, which contains an amino acid sequence of an endosulfine derived polypeptide. It also is within the scope of the present invention that different synthetic, recombinant or purified peptides identifying different epitopes of an endosulfine derived polypeptide can be used in combination in an assay to diagnose, evaluate, or prognose conditions associated with abnormal endosulfine production. In this case, these peptides can be coated onto one solid phase, or each separate peptide may be coated on separate solid phases, such as microparticles, and then combined to form a mixture of peptides which can be later used in assays. Furthermore, it is contemplated that multiple peptides which define epitopes from different polypeptides may be used in combination to make a diagnosis, evaluation, or prognosis of abnormal endosulfine production. To accomplish this, peptides coated on solid phases or labelled with detectable lables are allowed to compete with peptides from a patient sample for a limited amount of antibody. A reduction in binding of the synthetic, recombinant, or purified peptides to the antibody (or antibodies) is an indication of the presence of endosulfine-secreted polypeptides in the patient sample where it may not be expected (for example, in cerebral spinal fluid). Such variations of assay formats are known to those of ordinary skill in the art.

In another assay format, the presence of antibody and/or antigen to endosulfine derived polypeptide can be detected in a simultaneous assay, as follows. A test sample is simultaneously contacted with a capture reagent of a first analyte, wherein said capture reagent comprises a first binding member specific for a first analyte attached to a solid phase and a capture reagent for a second analyte, wherein said capture reagent comprises a first binding member for a second analyte attached to a second solid phase, to thereby form a mixture. This mixture is incubated for a time and under conditions sufficient to form capture reagent/first analyte and capture reagent/second analyte complexes. These so-formed complexes then are contacted with an indicator reagent comprising a member of a binding pair specific for the first analyte labeled with a signal generating compound and an indicator reagent comprising a member of a binding pair specific for the second analyte labeled with a signal generating compound to form a second mixture. This second mixture is incubated for a time and under conditions sufficient to form capture reagent/first analyte/indicator reagent complexes and capture reagent/second analyte/indicator reagent complexes. The presence of one or more analytes is determined by detecting a signal generated in connection with the complexes formed on either or both solid phases as an indication of the presence of one or more analytes in the test sample. In this assay format, recombinant antigens derived from human expression systems may be utilized as well as monoclonal antibodies produced from the proteins derived from the mammalian expression systems as disclosed herein. Such assay systems are described in greater detail in EP Publication No. 0473065.

In yet other assay formats, the polypeptides disclosed herein may be utilized to detect the presence of anti-endosulfine derived polypeptide in test samples. For example, a test sample is incubated with a solid phase to which at least one recombinant protein has been attached. These are reacted for a time and under conditions sufficient to form antigen/antibody complexes. Following incubation, the antigen/antibody complex is detected. Indicator reagents may be used to facilitate detection, depending upon the assay system chosen. In another assay format, a test sample is contacted with a solid phase to which a recombinant protein produced as described herein is attached and also is contacted with a monoclonal or polyclonal antibody specific for the protein, which preferably has been labeled with an indicator reagent. After incubation for a time and under conditions sufficient for antibody/antigen complexes to form, the solid phase is separated from the free phase, and the label is detected in either the solid or free phase as an indication of the presence of an endosulfine derived polypeptide antibody. Other assay formats utilizing the recombinant antigens disclosed herein are contemplated. These include contacting a test sample with a solid phase to which at least one antigen from a first source has been attached, incubating the solid phase and test sample for a time and under conditions sufficient to form antigen/antibody complexes, and then contacting the solid phase with a labeled antigen, which antigen is derived from a second source different from the first source. For example, a recombinant protein derived from a first source such as *E. coli* is used as a capture antigen on a solid phase, a test sample is added to the so-prepared solid phase, and a recombinant protein derived from a different source (i.e., non-*E. coli*) is utilized as a part of an indicator reagent. Likewise, combinations of a recombinant antigen on a solid phase and synthetic peptide in the indicator phase also are possible. Any assay format which utilizes an antigen specific for an endosulfine derived polypeptide from a first source as the capture antigen and an antigen specific for endosulfine derived polypeptide from a different second source are contemplated. Thus, various combinations of recombinant antigens, as well as the use of synthetic peptides, purified proteins, and the like, are within the scope of this invention. Assays such as this and others are described in U.S. Pat. No. 5,254,458, which enjoys common ownership and is incorporated herein by reference.

Other embodiments which utilize various other solid phases also are contemplated and are within the scope of this invention. For example, ion capture procedures for immobilizing an immobilizable reaction complex with a negatively charged polymer (described in EP publication 0326100 and EP publication No. 0406473), can be employed according to the present invention to effect a fast solution-phase immunochemical reaction. An immobilizable immune complex is separated from the rest of the reaction mixture by ionic interactions between the negatively charged polyanion/immune complex and the previously treated, positively charged porous matrix and detected by using various signal generating systems previously described, including those described in chemiluminescent signal measurements as described in EPO Publication No. 0 273,115.

Also, the methods of the present invention can be adapted for use in systems which utilize microparticle technology including in automated and semi-automated systems wherein the solid phase comprises a microparticle (magnetic or non-magnetic). Such systems include those described in published EPO applications Nos. EP 0 425 633 and EP 0 424 634, respectively.

The use of scanning probe microscopy (SPM) for immunoassays also is a technology to which the monoclonal antibodies of the present invention are easily adaptable. In scanning probe microscopy, in particular in atomic force microscopy, the capture phase, for example, at least one of the monoclonal antibodies of the invention, is adhered to a solid phase and a scanning probe microscope is utilized to detect antigen/antibody complexes which may be present on the surface of the solid phase. The use of scanning tunneling microscopy eliminates the need for labels which normally must be utilized in many immunoassay systems to detect antigen/antibody complexes. The use of SPM to monitor specific binding reactions can occur in many ways. In one embodiment, one member of a specific binding partner (analyte specific substance which is the monoclonal antibody of the invention) is attached to a surface suitable for scanning. The attachment of the analyte specific substance may be by adsorption to a test piece which comprises a solid phase of a plastic or metal surface, following methods known to those of ordinary skill in the art. Or, covalent attachment of a specific binding partner (analyte specific substance) to a test piece which test piece comprises a solid phase of derivatized plastic, metal, silicon, or glass may be utilized. Covalent attachment methods are known to those skilled in the art and include a variety of means to irreversibly link specific binding partners to the test piece. If the test piece is silicon or glass, the surface must be activated prior to attaching the specific binding partner. Also, polyelectrolyte interactions may be used to immobilize a specific binding partner on a surface of a test piece by using techniques and chemistries. The preferred method of attachment is by covalent means. Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not anticipated to alter the specific binding properties of the test piece.

While the present invention discloses the preference for the use of solid phases, it is contemplated that the reagents such as antibodies, proteins and peptides of the present invention can be utilized in non-solid phase assay systems. These assay systems are known to those skilled in the art, and are considered to be within the scope of the present invention.

It is contemplated that the reagent employed for the assay can be provided in the form of a test kit with one or more containers such as vials or bottles, with each container containing a separate reagent such as a probe, primer, monoclonal antibody or a cocktail of monoclonal antibodies, or a polypeptide (either recombinant or synthetic) employed in the assay. Other components such as buffers, controls, and the like, known to those of ordinary skill in art, may be included in such test kits. It also is contemplated to provide test kits which have means for collecting test samples comprising accessible body fluids, eg. blood, urine, saliva, and stool. Such collection means include lancets and absorbent paper or cloth for collecting and stabilizing blood; swabs for collecting and stabilizing saliva; cups for collecting and stabilizing urine or stool samples. Collection materials, papers, cloths, swabs, cups and the like, may optionally be treated to avoid denaturation or irreversible adsorption of the sample. The collection materials also may be treated with or contain preservatives, stabilizers or antimicrobial agents to help maintain the integrity of the specimens. Test kits designed for the collection, stabilization, and preservation of test specimens obtained by surgery or needle biopsy are also useful. It is contemplated that all kits may be configured in two components; one component for collection and transport of the specimen, and the other component for the analysis of the specimen. Further, kits for the collection, stabilization, and preservation of test specimens may be configured for use by untrained personnel and may be available in the open market for use at home with subsequent transportation to a laboratory for analysis of the test sample.

*E. coli* bacteria (clones 700415 and 384387) have been deposited at the American Type Culture Collection (A.T.C.C.), 12301 Parklawn Drive, Rockville, Md. 20852, as of Dec. 23, 1996, under the terms of the Budapest Treaty and will be maintained for a period of thirty (30) years from the date of deposit, or for five (5) years after the last request for the deposit, or for the enforceable period of the U.S. patent, whichever is longer. The deposit and any other deposited material described herein are provided for convenience only, and are not required to practice the present invention in view of the teachings provided herein. The cDNA sequence in all of the deposited material is incorporated herein by reference. Clones 700415 and 384387 were accorded A.T.C.C. Deposit No 97836 and 97835.

The present invention will now be described by way of examples, which are meant to illustrate, but not to limit, the scope of the present invention.

EXAMPLES

Example 1

Isolation of Full Length cDNA Clones of Human Endosulfine

Four partial amino acid sequences of porcine brain endosulfine (A. Virsolvy-Vergine, et al., (1996) supra) were used to generate a single consensus amino acid sequence for searching the LifeSeq™ human expression database (Incyte Pharmaceuticals, Inc., Palo Alto, Calif.) for human endosulfine sequences. The consensus sequence was generated by aligning the four porcine partial sequences with the amino acid sequence of bovine ARPP 19 (J. Girault, et al., *J. Neurosci.* 10: 1124–1133 (1990)) and filling in gaps between the partial sequences with the letter "x" (wherein x represented an unknown amino acid residue). A search performed with the consensus sequence (using both BLAST and Smith Waterman algorithms) identified several ESTs relating to either bovine ARPP19 and porcine α-endosulfine. Overlapping regions of the ESTs were aligned and the clones from two ESTs having the most 5' sequence relative to the other identified ESTs (i.e. clones 384387 and 700415) were selected for further study (see FIG. 1).

Figure 2A:
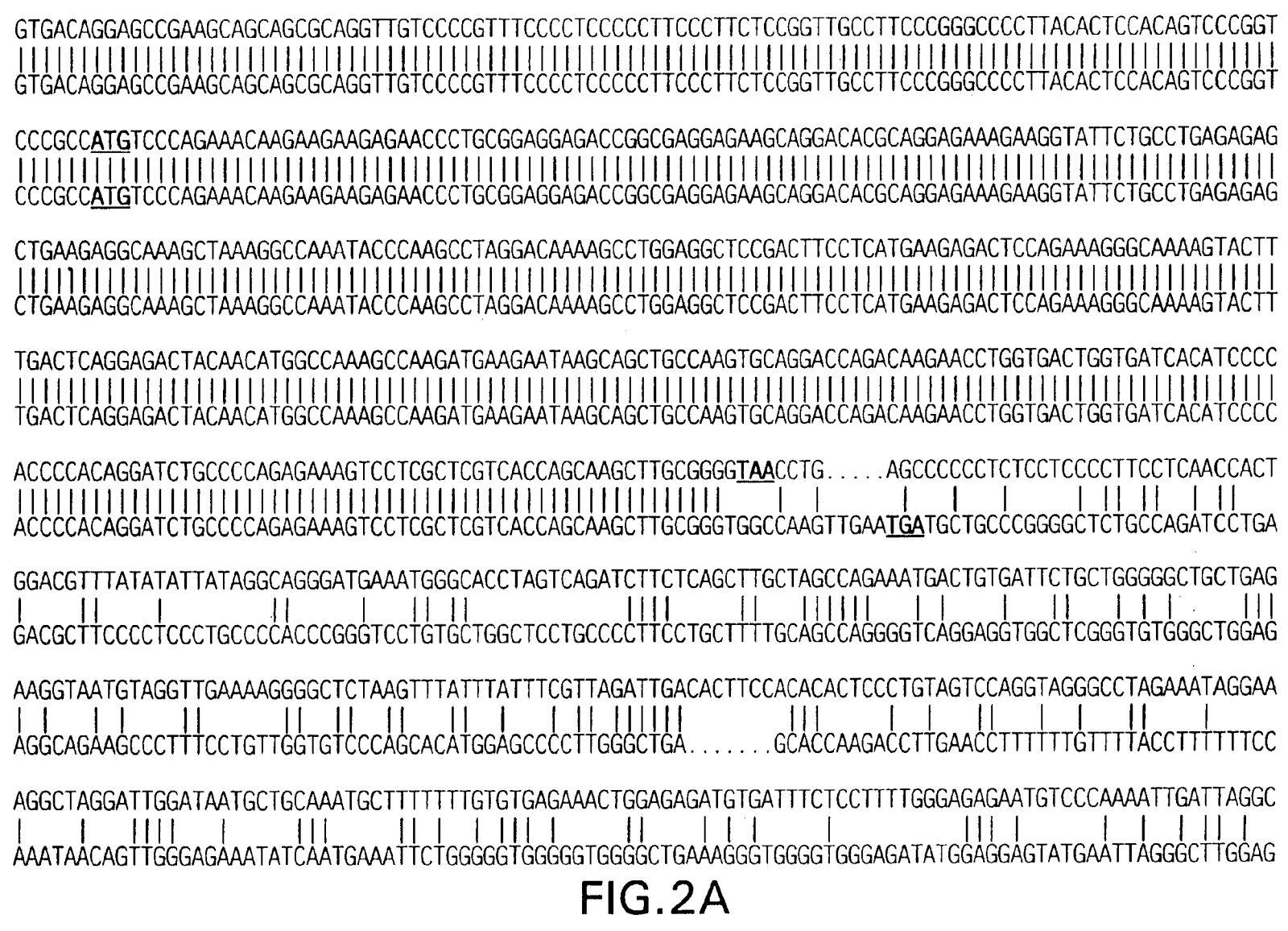

The cDNAs of clones 384387 and 700415 were amplified in bacteria and completely sequenced (SEQ ID NO:1 and SEQ ID NO:2 respectively, shown in FIG. 2). The deduced amino acid sequences of each clone showed clone 700415 to encode a polypeptide of 117 amino acids (SEQ ID NO:3) and clone 384387 to encode a polypeptide of 121 amino acids (SEQ ID NO:4) as shown in FIG. 3. Furthermore, both amino acid sequences displayed 100% homology in regions of overlap with the published partial sequence of bovine endosulfine and the consensus porcine α-endosulfine. The calculated molecular masses of the two proteins, based on the predicted amino acid sequences, were 12,975 and 13,389 Da, which is in agreement with the value obtained for porcine endosulfine (=13,196 Da as determined by mass spectrometry, see A. Virsolvy-Vergine, et al., (1996) supra).

To determine whether two full length clones encoding a human endosulfine had been identified, each of the cDNA inserts was subcloned into an expression vector, pcDNA3.1, (Invitrogen, San Diego, Calif.) and protein was produced in the presence of $^{35}$S-methionine using a TNT-coupled reticulocyte lysate transcription/translation kit from Promega (Madison, Wis.). The peptides produced were found to have an apparent molecular mass of 18 kDa (as determined by autoradiography following SDS-PAGE analysis on a 10% polyacrylamide gel, see FIG. 4), which is in agreement with the results of Virsolvy-Vergine et al. for porcine endosulfine (A. Virsolvy-Vergine, et al., (1996) supra). Our results suggested that the ATG initiation codon identified by sequence analysis was the authentic endosulfine initiation codon.

Example 2

Identification of Two Human Endosulfine Transcripts

The nucleotide sequences of the two endosulfine clones as well as the polypeptides deduced from each were compared to each other to determine the extent of sequence homology. Based on a comparison of the deduced amino acid sequences, it was found that the two clones encoded essentially identical polypeptides with the exception that clone 700415 encoded a polypeptide having four fewer amino acid residues than clone 384387. Comparative analysis of nucleotide sequences revealed that these clones had identical coding regions except for 12 nucleotides encoding the last four amino acids of clone 384387 (compare in FIG. 2 the top strand from nucleotide position 107 ("A" of ATG) to nucleotide position 457 and the bottom strand from nucleotide position 107 to nucleotide position 469). The 3' untranslated regions (3'-UTR, see FIG. 2 from the stop codons (bold-type TAA and TGA) to the end of each sequence) however, showed only 37% identity. These observations suggested that in humans, endosulfine could be present in at least two different isoforms, encoded by distinct mRNAs. To rule out the possibility that one of the two ESTs was a cloning artifact rather than a genuine endosulfine mRNA, primers were designed (for use in reverse transcription PCR (rt-PCR) experiments) which would distinguish the presence of each clone on the basis of product size. The sequences of the primers used for rt-PCR are shown below in Table 1.

TABLE 1

| Type | SEQUENCE | SEQ ID NO |
|---|---|---|
| Forward (F) | 5'- GAAGAGACTCCAGAAAGGGC -3' | SEQ ID NO: 5 |
| Reverse for endosulfine A (RA) | 5'- GAAGCAATAGCAGCCTAAGG -3' | SEQ ID NO: 6 |
| Reverse for endosulfine B (RB) | 5'- TGTGCTGGGACACCAACAG -3' | SEQ ID NO: 7 |

Figure 5:
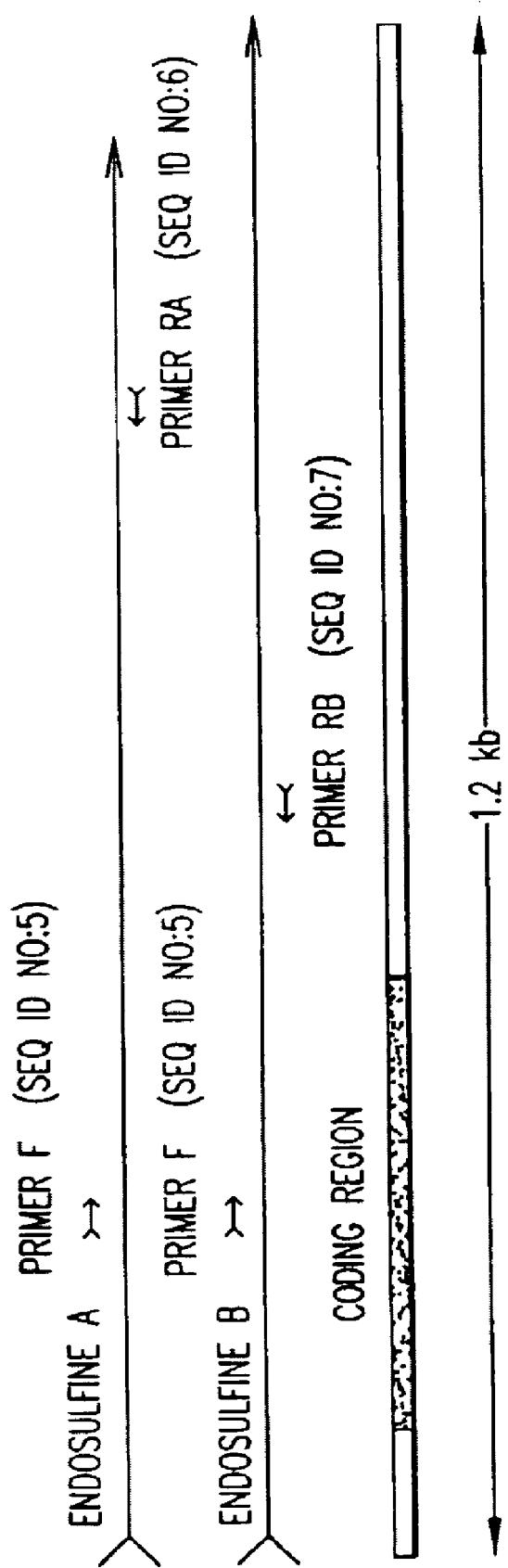
FIG. 5 diagrammatically shows the positions of a forward primer (SEQ ID NO:5) and two reverse primers (SEQ ID NO:6 and SEQ ID NO:7) with respect to the templates (endosulfine A and endosulfine B cDNA) used to generate PCR products specific for endosulfine A and endosulfine B. The forward primer is complementary to the same nucleotide sequence of the endosulfine A and endosulfine B genes (i.e. it is complementary to a sequence in the coding region of these genes). The reverse primers are complementary to different sequences in the 3'-untranslated region the endosulfine A and endosulfine B genes.

SEQ ID NO:5 was designed to hybridize to identical regions of both clones (i.e. within the coding region, see FIG. 5) and corresponds to nucleotide positions 271–290 of both SEQ ID NO:1 and SEQ ID NO:2. SEQ ID NO:6 and SEQ ID NO:7 were designed to hybridize to the 3' UTRs of clones 700415 and 384387 (also see FIG. 5) and correspond to nucleotide positions 904–923 in SEQ ID NO:1 and nucleotide positions 617–635 in SEQ ID NO:2. As a consequence of these designs, a 365 bp nucleotide product was expected to be generated from amplification of clone 384387 with the SEQ ID NO:5 and SEQ ID NO:7 primers. In contrast, amplification of clone 700415 cDNA with SEQ ID NO:5 and SEQ ID NO:6 was expected to produce a nucleotide product of 653 bp.

To ascertain whether the primer sets would in fact generate PCR products of these sizes, PCR reactions were first performed using each primer set with its corresponding template DNA under standard PCR conditions (i.e. in a total reaction volume of 50 μL containing 200 μM of each dNTP wherein N was A, T, G and C, 0.4 μM of each primer (i.e. 0.4 μM of SEQ ID NO:5 with either 0.4 μM of SEQ ID NO:6 or 0.4 μM of SEQ ID NO:7), 250 ng template DNA and 1 unit of pfu enzyme (Stratagene, La Jolla, Calif.)). Template DNA was denatured at 94° C. for 5 minutes prior to initiating a PCR reaction. Amplifications were performed for a total of 40 cycles (1 cycle=94° C. for 30 seconds, 55° C. for 45 seconds, and 72° C. for 2 minutes), followed by one final extension step of 7 minutes at 72° C. As a negative control, each primer pair was amplified as described above but using DNA from the opposite clone as a template. As expected, amplification of a sequence of 384387 cDNA using primers SEQ ID NO:5 and SEQ ID NO:7 produced a product of approximately 365 bp (see FIG. 6, left panel, lane D) whereas amplification of a sequence of 700415 cDNA using primers SEQ ID NO:5 and SEQ ID NO:6 produced a product of approximately 653 bp (see FIG. 6, left panel, lane A). In contrast, no product was produced when 700415 cDNA was amplified using SEQ ID NO:5 and SEQ ID NO:7 or when 384387 cDNA was amplified using SEQ ID NO:5 and SEQ ID NO:6 as primers (see FIG. 6, left panel, lanes B and C respectively). These results demonstrated that each primer set specifically hybridized to its corresponding template and not to the other template.

Figure 6:
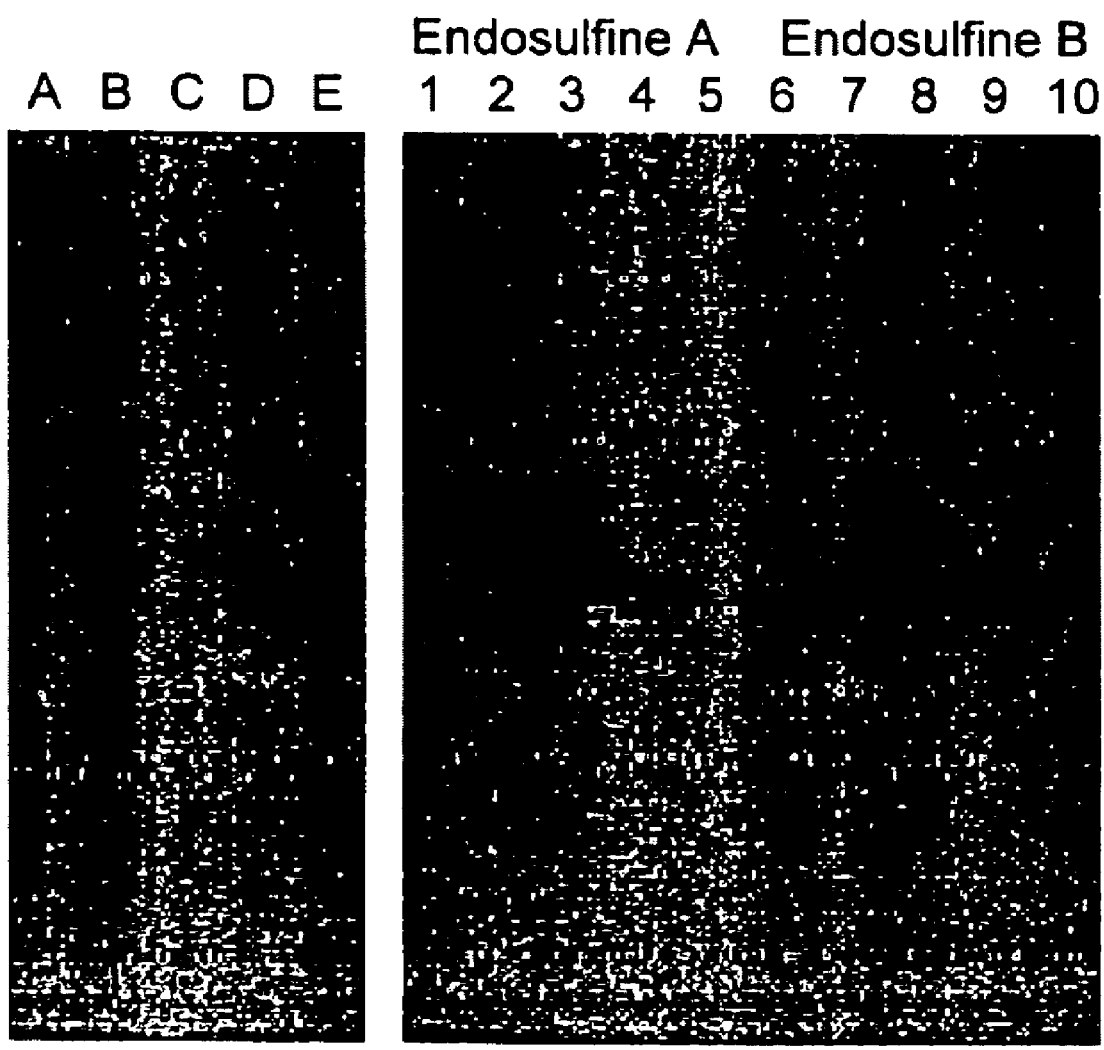
FIG. 6 shows computer generated images of PCR products electrophoresed on 1.2% agarose gels in TAE buffer and stained with ethidium bromide. The left panel illustrates PCR products obtained when plasmids carrying cDNAs of endosulfine A (lanes A and B) and endosulfine B (lanes C and D) were used as templates in PCR experiments with primer pairs SEQ ID NO:5/SEQ ID NO:6 (lanes A and C) and SEQ ID NO:5/SEQ ID NO:7 (lanes B and D). Molecular weight standards are shown in lane E.

The two primer pairs were then used in rt-PCR experiments with human poly A⁺ RNA from various brain regions and pancreas to determine whether two transcripts could be detected. For all tissues tested, poly A+ RNA was denatured for 5 minutes at 80° C., then reverse-transcribed for 1 hour at 37° C. using random hexamers (as primer) and Superscript II reverse transcriptase (Life Technologies, Gaithersburg, Md.). PCR was carried out as described above using the DNA from each tissue type as a template for both sets of primers. The PCR products were separated by electrophoresis in 1.2% agarose gel in TAE (Tris-Acetate-EDTA) buffer and detected by UV fluorescence after staining in a solution of ethidium bromide/TAE (0.5 μg/mL). As the right panel in FIG. 6 shows, both the 365 bp (lanes 6–10) and 653 bp (lanes 1–5) products were generated when cDNAs from brain (lanes 1 and 6), cerebellum (lanes 2 and 7), fetal brain (lanes 3 and 8), pancreas (lanes 4 and 9) and substantia nigra (lanes 5 and 10) were amplified. This data confirmed the presence of at least two transcripts for human endosulfine in these tissues.

Using the Peptidesort program (University of Wisconsin GCG Program, Madison, Wis.), the predicted isoelectric points were found to be 8.9 for the shorter form (encoded by clone 700415) and 7.5 for the longer form (encoded by clone 384387). The shorter form was named endosulfine A and the longer form, endosulfine B.

Example 3

Localization of Endosulfine Transcripts in Human Tissues

The well known technique of Northern blotting provides for the detection of messenger RNA and gives a reasonable estimation of its size and steady-state level in a particular tissue (Sambrook et al., supra). Multiple Tissue Northern Blots were purchased from Clontech (Palo Alto, Calif.) and probed with an endosulfine cDNA fragment corresponding to the first 190 nucleotides of the endosulfine cDNA (i.e. from nucleotide position 1 to nucleotide position 190). This fragment was labeled with $\alpha$-$^{32}$P-dCTP by random priming using a commercial labeling kit (Stratagene, La Jolla, Calif.) to a specific activity of $1.1 \times 10^9$ cpm/mg DNA. The blots (membranes) were prehybridized at 60° C. for 1 hour in Express Hyb solution (supplied with the kit) and hybridized (also in Express Hyb solution) at the same temperature for two hours in the presence of denatured probe at $2 \times 10^6$ cpm/mL. After washing the blots twice in 2×SSC+0.5% SDS (20 min each wash), and twice under stringent conditions (0.1×SSC+0.01% SDS, 50° C., 20 min. each wash), the filters were exposed to a phosphorimager screen. Two messages of approximate sizes 1.5 and 3.5 kb were detected (see FIG. 7). The small message (1.5 kb) was present in all tissues examined, although at extremely low levels in liver and testis, and was barely detectable in lung. The large message (3.5 kb) was expressed at a lower level in most tissues examined, with the exception of skeletal muscle (highest level of expression) and testis and was undectable in leukocytes, lung, and liver. These results suggested that mRNA species for endosulfine are present in a variety of tissues. Furthermore, the differences in relative abundance of the two messages in the different tissues, suggested that transcription is differentially regulated.

Example 4

Ribonuclease Protection Assay

Alternatively, instead of or in addition to performing a Northern blot as described in Example 3, a ribonuclease protection assay may be performed as follows:

A. Labeling of Complementary RNA (cRNA) Hybridization Probes. Labeled sense and antisense riboprobes are transcribed from the EST sequence which contains an RNA polymerase promoter such as SP6 or T7. The sequence may be from a vector containing the appropriate EST insert or from a PCR-generated product of the insert using PCR primers which incorporate am RNA polymerase promoter sequence. The transcripts are prepared in a 20 μL reaction volume containing 1 μg of DNA template, 2 μL of 100 mM dithiothreitol, 0.8 μL of RNasin (10–40 U), 500 μM each of ATP, CTP, GTP, 5 μL (alpha$^{32}$P) UTP or 100–500 μM biotinylated UTP, and 1 μL of RNA polymerase in transcription buffer (40 mM Tris-HCl, pH 7.5, 6 mM MgCl$_2$, 2 mM spermidine HCl, 5 mM NaCl). Following incubation at 37° C. for one hour, the transcripts are treated with DNase 1 (15 U) for an additional 30 min to digest the template. The probes then are isolated by spin columns, salt precipitation or electrophoresis techniques which are well-known in the art. Finally, the probes are dissolved in lysis buffer (5 M Guanidine Thiocyanate, 0.1 M EDTA, pH 7.0).

B. Hybridization of Labeled Probe to Target. Approximately 20 μg of extracted total cellular RNA, prepared as described in Sambrook, et al. supra, is placed in 10 μL of lysis buffer and mixed with either (i) $1 \times 10^5$ cpm of radioactively labeled probe or (ii) 250 pg of non-isotopically labeled probe, each in 2 μL of lysis buffer. The mixture then is incubated at 60° C. for 5 min and hybridized overnight at room temperature. See, T. Kaabache et al., *Anal. Biochem.* 232: 225–230 (1995).

C. RNase Digestion. Hybridizations are terminated by incubation with 380 μL of a solution containing 40 μg/mL RNase A and 625 U/mL RNase T1 in 1 mM EDTA, 300 mM NaCl, 30 mM Tris-HCl pH 7.4 for 45–60 min at room temperature. RNase digestion then is terminated by the addition of 60 μL of proteinase-K (1.7 mg/mL) containing 3.3% SDS, followed by incubation for 30 min at 37° C. The digested mixture then is extracted with phenol:chloroform:isoamyl alcohol to remove protein. The mRNA:cRNA hybrids are precipitated from the aqueous phase by the addition 4 μg yeast tRNA and 800 μL of ethanol, and incubation at −80° C. for 30 min. The precipitates are collected by centrifugation.

D. Fragment Analysis. The precipitates are dissolved in 5 μL of denaturing gel loading dye (80% formamide, 10 mM EDTA, pH 8.0, 1 mg/mL xylene cyanol, 1 mg/mL bromophenol blue) and electrophoresed in 6% polyacrylamide TBE, 8 M urea denaturing gels. The gels are dried under vacuum and autoradiographed. Quantitation can be performed by comparing the counts obtained from the test samples to a calibration curve that was generated by utilizing calibrators that are the sense strand. In cases where non-isotopic labels are used, hybrids are transferred from the gels to membranes (nylon or nitrocellulose) by blotting and then analyzed using detection systems that employ streptavidin alkaline phosphatase conjugates and chemiluminesence or chemifluoresence reagents. Again, expression of an mRNA which is detectable by the labeled probe in a particular tissue suggests that endosulfine is produced in that tissue.

Example 5

Identification of Additional Members of the Endosulfine Family

The Northern blot method described in Example 3 supra can detects distinct messages only if they have large differences in sizes (more than 100 to 200 nucleotides); small differences in message size (such as those arising from alternative splicing in the coding region) are not detected by this method. Instead, other strategies are used to detect possible variants of endosulfine message and determine their steady-state levels. Splice variants in the coding region can be detected by rt-PCR using primers designed to give products of small size. In the case of endosulfine, the coding region is small enough (351 to 363 bp) to be covered in one single experiment with primers at each extremity. Variants in the 3' UTR can also be detected by rt-PCR. In rt-PCR, the forward primer is chosen in a region of the ORF that is common to all message variants known so far, as close as possible to the stop codon. The reverse primer is an oligo-dT anchored with a dinucleotide for the specificity. Since the first nucleotide of the anchor can be A, C, or G, and the second nucleotide can be either A, C, G, or T, a combination of 12 anchored reverse primers are needed. Each reverse primer is thus used with the unique forward primer, in 12 different reactions. The PCR products are then run in an agarose gel and detected by UV fluorescence after ethidium bromide staining. Because of its high sensitivity and specificity, this method allows the detection of even small size and sequence variations in the 3' UTR.

Example 6

Dot Blot/Slot Blot

Dot and slot blot assays are quick methods to evaluate the presence of a specific nucleic acid sequence in a complex mix of nucleic acid.

To perform, up to 20 µg of RNA is mixed in 50 µL of 50% formamide, 7% formaldehyde, 1×SSC, incubate 15 min at 68° C. and cool on ice. Then, 100 µL of 20×SSC is added to the RNA mixture and loaded under vacuum onto a manifold apparatus that has a prepared nitrocellulose or nylon membrane. The membrane is soaked in water, 20×SSC for 1 hour, placed on two sheets of 20×SSC prewet Whatman #3 filter paper, and loaded into a slot blot or dot blot vacuum manifold apparatus. The slot blot is analyzed with probes prepared and labeled as in Example 4 supra.

Other methods and buffers not specifically detailed for Examples 3–5 are described in J. Sambrook et al., supra.

Example 7

In Situ Hybridization

This method is useful to directly detect specific target nucleic acid sequences in cells using detectable nucleic acid hybridization probes.

Tissues are prepared with cross-linking fixatives agents such as paraformaldehyde or glutaraldehyde for maximum cellular RNA retention. See, L. Angerer et al., Methods in Cell Biol. 35: 37–71 (1991). Briefly, the tissue is placed in greater than 5 volumes of 1% glutaraldehyde in 50 mM sodium phosphate, pH 7.5 at 4° C. for 30 min. The solution is changed with fresh solution for a further 30 min fixing. The fixing solution should have an osmolality of approximately 0.375% NaCl. The tissue is washed once in isotonic NaCl to remove the phosphate.

The fixed tissues then are embedded in paraffin, as follows. The tissue is dehydrated through a series of ethanol concentrations for 15 min each: 50% twice, 70% twice, 85%, 90% and 100% twice. The tissue next is soaked in two changes of xylene for 20 min each at room temperature; then it is soaked in two changes of 1 xylene: 1 paraffin for 20 min each at 60° C., and then it is soaked in three final changes in paraffin for 15 min each.

The tissue next is cut in 5 µm sections using a standard microtome and placed on a slide previously treated with the tissue adhesive 3-aminopropyltriethoxysilane.

Paraffin is removed from the tissue by two 10 min xylene soaks and rehydrated in a series of ethanol concentrations; 99% twice, 95%, 85%, 70%, 50%, 30% and distilled water twice. The sections are pre-treated with 0.2 M HCl for 10 min and permeabilized with 2 µg/mL Proteinase-K at 37° C. for 15 min.

Labeled riboprobes transcribed from the pSPORT1 plasmid containing fragments of endosulfine cDNA are hybridized to the prepared tissue sections and hybridized overnight at 56° C. in 3× standard saline extract and 50% formamide. Excess probe is removed by washing in 2× standard saline citrate and 50% formamide followed by digestion with 100 µg/mL RNase A at 37° C. for 30 min. Fluorescence probe is visualized by illumination with UV light under a microscope. Fluorescence in the cytoplasm is indicative of mRNA production. Fluorescence in the nucleus detects the presence of genomic material. Alternatively, the sections can be visualized by autoradiography.

Example 8

Bacterial Expression and Purification of Endosulfine A and B

A. Construction of Expression Vectors containing DNA Fragments Encoding Endosulfine A and B: DNA fragments encoding endosulfine A and B were generated by PCR for introduction into a prokaryotic expression vector, pProExI, (Life Technologies, Gaithersburg, Md.) using clones 700415 or 384387 as template DNA and the following primers:

| SEQUENCE (5'---->3') | SEQ ID NO: | Template (clone #) |
|---|---|---|
| GGAAGGCGCC*ATG*TCCCAGAAACAAGAAG | SEQ ID NO: 8 | 700415, 384387 |
| CAAAGTCGAC*TTA*CCCCGCAAGCTTGCTG | SEQ ID NO: 9 | 700415 |
| CCAAGTCGAC*TCA*TTCAACTTGGCCACCC | SEQ ID NO: 10 | 384387 |

In order to perform in-frame translational and directional ligation, the 5' forward primer (SEQ ID NO:8) was synthesized to create an EheI restriction site (shown in bold type and underlined) immediately upstream of the ATG initiation codon (shown in italic type). Similarly, each reverse primers (i.e. SEQ ID NO:9 for endosulfine A and SEQ ID NO:10 for endosulfine B), was synthesized to create a SalI restriction site (also shown in bold type and underlined) immediately downstream of the TTA and TCA stop codons respectively (also shown in italics). PCR was performed as described in Example 2. After amplification, the PCR products were digested with EheI and SalI, gel purified, and ligated into pProExI, (previously digested with the same restriction enzymes) using standard ligation techniques (see J. Sambrook, et al. supra). *E. coli* DH5∝ cells were then transformed with the ligation mixtures and selected on medium containing ampicillin. Plasmid DNA was prepared from individual clones and subjected to restriction enzyme analysis using PvuII to confirm that endosulfine A or B inserts were in the proper orientation.

B. Purification of His-tagged Endosulfine A and B: In the pProExI expression system, a desired protein is produced with a tag of six histidine residues fused upstream of the protein. Accordingly, the pProExI vectors containing the cloned endosulfine A and B genes were expected to produce fusion proteins of his-tagged endosulfine A or B which could be purified by affinity chromatography to a nickel-conjugated resin. To produce the fusion proteins for purification, recombinant bacteria (carrying either the endosulfine A or B expression vector) were grown overnight in Luria broth containing 50 μg/mL ampicillin (LB+amp) on a rotary shaker at 225 rpm, at 37° C. and used to inoculate fresh LB+amp (300 mL) at a 1:10 dilution. The fresh cultures were incubated, with shaking at 225 rpm, at 37° C. for 1 hour, induced with isopropyl β-D-thiogalactopyranoside (IPTG, 1 mM) and re-incubated for an additional 3 hours. Cultures were then centrifuged at 5,000 g to pellet the bacteria. Pellets were resuspended in 10 mL of lysis buffer (50 mM sodium phosphate (pH 8.0), 0.3 M NaCl, 1 mM phenylmethylsulfonyl fluoride (PMSF), and 0.2 mM benzamidine) containing 1% TRITON-X100 at 4° C. and sonicated on ice until greater than 90% of the cells had been lysed (as determined by $OD_{590}$). After sonication, cell debris and unlysed cells were removed by centrifugation at 10,000 g for 10 minutes at 4° C. The resulting supernatant was loaded onto a 3 mL bed volume nickle-nitro-triacetic acid (Ni-NTA) column (QIAGEN, Chatsworth, Calif.) which had been pre-equilibrated with 10 bed volumes of lysis buffer containing 0.1% TRITON-X100. The column was sequentially washed with 10 bed volumes of wash buffer (50 mM sodium phosphate, pH 6.0, 0.3 M NaCl, and 0.1% TRITON-X100) and 10 bed volumes of 50 mM imidazole in the same buffer (to remove non-specifically bound proteins). The his-tagged endosulfine fusion proteins were eluted from the column with a total of 5 bed volumes of wash buffer containing 0.2 M imidazole and collected as 2 mL fractions. The purity of each eluted fusion protein was assessed after SDS-PAGE on a 13.5% gel which was stained with Coomassie blue (see FIG. 8). The protein concentration was determined by absorbance at 280 nm after determining the relative extinction coefficients for each of the recombinant fusion proteins.

Example 9

Cloning and Expression of Endosulfine A and B in Eukaryotic Cells

Endosulfine A and B cDNAs were cut from their parent vectors (pSPORT1, Life Technologies, Gaithersburg, Md. and pBS-SK+, Stratagene, La Jolla, Calif.) by digestion with EcoRI and XbaI (for endosulfine A) and EcoRI and XhoI (for endosulfine B) to produce fragments of 1.15 kb and 1.25 kb, respectively. Each fragment was gel purified and ligated into the mammalian expression vector, pcDNA3.1, (Invitrogen, San Diego, Calif.) previously cut with the same enzymes. Ligated DNAs were transformed into *E. coli* DH5α cells and recombinant clones selected for ampicillin resistance. Plasmid DNA was prepared from individual clones and subjected to restriction enzyme analysis to identify recombinant clones containing endosulfine A or B insert DNA in the proper orientation. Two such clones were found and termed pCMVEsA2 (for endosulfine A) and pCMVEsB5 (for endosulfine B).

Expression of endosulfine A and B in mammalian cells may be achieved by a procedures well known in the art, such as lipofection. To perform lipofection, cells (such as HEK293) are grown in tissue cultures plates in an appropriate growth medium such as Dulbecco's Modified Eagle's Medium (DMEM) or RPMI 1640 medium (Gibco, BRL, Gaithersburg, Md.) supplemented with 10% fetal bovine serum, 100 U/mL penicillin, 100 mg/mL streptomycin and 0.25 mg/mL amphotericin B under conditions suitable for growth (i.e. in a humidified atmosphere containing 5% $CO_2$ at 37° C.) to approximately 50%–60% confluence. Afterwards, approximately 1–2×10⁶ cells are transfected with a mixture of DNA (1.5 mg) and lipofectamine (20 mg) in 5mL Optimem (Life Technologies, Gaithersburg, Md.) in 100 mm dish and incubated for forty eight hours. The cells are split 1:10 or 1:20 in fresh growth medium and again incubated as described above. Once the cells have adhered to the plates, the growth medium is replaced with selection medium (growth medium containing the antibiotic geneticin at 400–500 μg/mL), in order to select for neomycin-resistant clones. Cells are then incubated under the standard growth conditions described above for 2–3 weeks, with periodic replacements of the selection medium, after which antibiotic-resistant clones are picked for further propagation and analysis.

Example 10

Production of Synthetic Peptides of Endosulfine A and B

Synthetic peptide sequences are selected from the conserved N-terminal region of human endosulfine A and B encompassing amino acids 1–27. Peptides are synthesized on an ABI Peptide Synthesizer (available from Applied Biosystems, Foster City, Calif.), Model 431A, using standard reagents and conditions known in the art for solid phase peptide synthesis (see for example, Stewart, J. M., and Young, D. J., *Solid Phase Peptide Synthesis*, W. H. Freeman Co., San Francisco, 1963). Briefly, a peptide sequence is generated on a resin (such as chloromethyl-polystyrene-divinylbenzene) by the sequential coupling of one or more amino acids or suitably protected amino acids to a growing peptide chain. Cleavage of the peptide from the resin and final deprotection of the peptide are achieved by adding the resin to 20 mL trifluoroacetic acid (TFA), 0.3 mL water, 0.2 mL ethanedithiol, 0.2 mL thioanisole and 100 mg phenol, and stirring at room temperature for 1.5 hours. The resin then is filtered by suction and the peptide obtained by precipitation of the TFA solution with ether, followed by filtration. Each peptide is purified via reverse-phase preparative HPLC using a water/acetonitrile/0.1% TFA gradient and lyophilized. The product is confirmed by mass spectrometry.

Example 11

Production of Polyclonal Antibodies to Endosulfine A and B

A. Preparation of Immunizing Antigens: Purified synthetic peptides are prepared as described in Example 10. To generate antigens for immunization, the purified peptides are conjugated to Keyhole Limpet Hemocyanin (KLH) and bovine serum albumin (BSA) using an Imject Activated Immunogen Conjugation Kit (Pierce, Rockford, Ill.) in accordance with the manufacturer's instructions.

B. Immunization Protocol: Polyclonal antisera are generated using the protocol of the Berkeley Antibody Company (Berkeley, Calif.). Before receiving the first immunization, a sample of preimmune blood (5 mL) is drawn from each of at least 2 rabbits. Afterward, each rabbit is injected subcutaneously with an aliquot of KLH-conjugated peptide (200–500 µg) in Complete Freunds Adjuvant. After 21 days, the immune response is boosted with a second subcutaneous injection of KLH-conjugated peptide (100–250 µg) in Incomplete Freund's Adjuvant. Blood (50 mL) is collected on day 31 and serum tested for reactivity to BSA-coupled peptide using an enzyme linked immunoadsorbant assay (ELISA). Subsequent boosts with KLH-conjugated peptide are given on days 42, 63 and 84 (post injection #1) and production bleeds (50 mL) drawn on days 52, 73 and 94 for testing by ELISA in the manner described. Serum is then stored at −20° C. until further use.

Example 12

Modulation of ATP-Sensitive Potassium Channels by Endosulfine A and Endosulfine B A. Inhibition of [$^3$H]-Glyburide Binding with Purified Endosulfine A and B: To investigate the interaction between sulfonylurea receptors and endosulfine A and B, competition studies are performed using his-tagged endosulfine A and B fusion proteins prepared as in Example 8. Aliquots (150 µg) of brain P2 membranes (obtained from ABS Inc., Willmington, Del.) are incubated for 60 min at 22° C. in 50 mM Tris-HCl, pH 7.2 in the presence of 0.32 nM [$^3$H]-glyburide and with increasing concentrations (0.01 nM–10 mM) of unlabeled purified recombinant endosulfine A and B. Bound [$^3$H]-glyburide is determined by filtration on GF/B filters on a Skatron Cell Harvester (Skatron Instruments, Sterling, Va.), followed by scintillation counting in a LKB Wallac Inc. scintillation counter Model number 1205, Gaithersburg, Md.

B. Rubidium flux assay: The ability of endosulfine A or B to modulate $^{86}$Rb$^+$ efflux is determined either in cell lines stably expressing recombinant SUR/Kir combinations or cell lines already known to express ATP-sensitive K$^+$ channels (such as RIN5mF, βTC or HIT cells). To determine if endosulfine A or B are inhibitors or activators of ATP-sensitive K$^+$ channels, cells are loaded with $^{86}$RbCl$_2$ and assayed for inhibition or induction of $^{86}$RbCl$_2$ efflux. In both cases, the cell culture and $^{86}$RbCl$_2$ loading is performed in the same manner. Briefly, the cells (typically RIN5mF cells; available from the A.T.C.C., 12301 Parklawn Drive, Rockville, Md.) are plated in a 24-well plate and maintained in an appropriate media supplemented with 10% Fetal Calf Serum, 100 U/mL pen/strep/0.25 mg/mL amphotericin and 2 mM L-glutamine (Life Technologies, Gaithersburg, Md.) at 37° C. in a humidified atmosphere of 10% CO$_2$. When the cells have proliferated to form a confluent monolayer, the old media is replaced with media containing 0.1 µCi $^{86}$RbCl/well (NEN-Dupont, Willmington, Del.) and incubated at 37° C. for five hours.

1. Activation of $^{86}$Rb$^+$ Efflux by endosulfine A or B: The $^{86}$RbCl$_2$ containing media is removed by aspiration and the cell monolayer is washed twice with a buffer containing 20 mM Hepes.NaOH, pH 7.4, 120 mM NaCl, 7 mM KCl, 2 mM CaCl$_2$, 1 mM MgCl$_2$, 30 mM ouabain (to inhibit the Na$^+$-K$^+$ pump) to remove unincorporated $^{86}$RbCl$_2$. The same buffer containing endosulfine A or B (1 pM–20 µM) is added to the monolayer in a volume of 210 µL and incubated in a humidified atmosphere for 30 min. Radioactivity present in the cell supernatant is subsequently quantified by gamma counting for 1 min in a 1440 Wizard automatic gamma counter (Wallac, Gaithersburg, Md.). Results are analyzed relative to the controls.

2. Inhibition of $^{96}$Rb$^+$ Efflux: The cells are loaded with $^{86}$RbCl$_2$ in the presence of 6 mM glucose and then treated with metabolic inhibitors, i.e. 1 mM 2-deoxyglucose or oligomycin (0.24 ug/mL) to induce $^{86}$Rb efflux for 30 min in the presence or absence of endosulfine A and B (1 pM–20 uM). The efflux is quantified by gamma counting as above.

Example 13

Neuroprotection of Glutamate Treated Neurons by Endosulfine A or B

A. Primary Cell Culture: Hippocampal and cortical primary cultures are prepared from Sprague-Dawley rat fetuses (Charles River, Wilmington, Mass.) at day 18 of gestation. Fetuses are dissected from the uterus, decapitated and their heads placed in a 100 mm dissecting dish containing Leibovitz L-15 media (Life Technologies, Gaithersburg, Md.). The brain is dissected from each head and the blood vessels and meninges are removed. For cortical culture preparations, only the cortex is dissected from the brain and used for further processing; for hippocampal cultures, the cerebral hemispheres are separated from the diencephalon and brainstem, and the hippocampi dissected from each hemisphere. Tissue is transferred to a 15 mL conical tube, an equal volume of trypsin (0.25%, Life Technologies, Gaithersburg, Md.) is added and the solution incubated at 37° C. for 15 minutes. Trypsin is removed by pelleting the cells at 200 g for 15 min and decanting the supernatant. The pelleted cells are dissociated by tituration after adding 5 mL of Dulbecco's Modified Eagle Medium (DMEM) supplemented with 10% Fetal Calf Serum (FCS)/25 mM glucose/4 mM glutamine/50 Units/mL pen:strep/B27. The cell suspension is then passed through a 143 mm nylon membrane and cell density determined by counting a sample of trypan blue stained cells. Cells are then plated at a density of 50,000 cells/well in 96-well microtiter plates (pre-coated with a solution of poly-L-lysine (0.033 mg/mL) and rinsed with sterile water prior to use) and maintained at 37° C. in a humidified atmosphere of 10% CO$_2$. After 24 hours, the FCS supplemented DMEM is removed and replaced with supplemented DMEM lacking FCS.

B. Neuroprotection Assay: Cells are maintained for 5–6 days in vitro before the media is removed and replaced with DMEM/N2 supplement (Life Technologies, Gaithersburg, Md.) containing concentrations of test compound (such as endosulfine A or B) ranging from 1 fM to 1 mM. After incubating for 2 hours, an equal volume of the DMEM/N2 supplement containing 7.2 mM CaCl$_2$ and 1 mM L-Glutamate is added to each well (final concentrations=3.6 mM and 500 µM of CaCl$_2$ and L-Glutamate respectively) and the cells reincubated for 15 minutes. This solution is removed, replaced with DMEM/N2 supplement and the cells reincubated for 24 hours. Neuronal death is quantified using a Cytotox 96™ assay kit (Promega Corporation, Madison, Wis.) which measures the amount of lactate dehydrogenase (LDH), released into the medium. This enzyme converts tetrazolium salt into a red formazen product (which is measurable with a spectrophotometer at 490 nm) in an amount proportional to the number of lysed cells.

The amount of basal LDH release is calculated as a percentage of LDH released upon lysis of the cells with 10% Triton X-100 (Sigma, St. Louis, Ill.) and usually amounts to 5–10% of the total LDH released. Glutamate treatment of cells usually results in a 2–3 fold increase of LDH release over basal levels. All LDH release values determined for cells exposed to test compounds are normalized to 500 µM glutamate induced death as the maximum (100%) on each plate. LDH values from neurons exposed to compounds that protect neurons from the effects of glutamate will be lower than control LDH values.

Example 14

Modulation of Insulin Release by Human Endosulfine A or B

The ability of endosulfine A or B to modulate insulin release is firstly evaluated in cells that are already known to release significant amounts of insulin (such as for example, βTC cells derived from a transgenic mouse insulinoma (A.T.C.C., 12301 Parklawn Drive, Rockville, Md.)). Secondly, the ability of endosulfine A or B to stimulate insulin secretion is assessed on cells that secrete low levels of insulin such as RINm5F cells (derived from a rat insulinoma). Finally, the role of endosulfine A or B in insulin secretion from the βTC cells is further assessed by reducing the levels of endosulfine A or B expressed in these cells using antisense (see Example 16).

A. Cell culture: Both named cell lines are routinely grown in Dulbecco's Modified Eagle Medium (DMEM) containing 25 mM glucose and supplemented with 10% (v/v) fetal calf serum, 100 U/mL of penicillin, and 100 μg/mL of streptomycin. Confluent cells are split for subculture 1:4 weekly and media is changed twice weekly.

B. Insulin Secretion Cells are plated in 12-well culture dishes (Costar, Cambridge, Mass.) at $4 \times 10^5$/well. Studies are performed 4–6 days after plating, when the cells are 70–90% confluent. The medium is exchanged with fresh medium 16 hours before secretion studies. To perform the experiment, the medium is removed, and the cells are washed twice with HEPES-buffered Krebs-Ringer (119 mM NaCl, 4.74 mM KCl, 2.54 mM $CaCl_2$, 1.19 mM $MgSO_4$, 1.19 mM $KH_2PO_4$, 25 mM $NaHCO_3$, 10 mM HEPES at pH 7.4, and 0.1% BSA, bubbled with 5% $CO_2$; incubation buffer). They are then preincubated with the same buffer at 37° C. for 1 hour, after which the buffer is removed. Incubations are performed in 3 mL incubation buffer, with or without the addition of endosulfine A or B, for up to 120 min. At the end of the incubation period the buffer is removed and centrifuged at 400 g to remove any detached cells, and the supernatant is assayed for insulin. Insulin levels in the medium are assayed by radioimmunoassay (RIA) using guinea pig anti-insulin serum, with monoiodinated porcine insulin as a tracer and rat insulin as a standard.

It is understood that the conditions and reagents under which the assay is performed (such as cell growth conditions, media, buffers etc.) may be optimized or altered.

Example 15

Modulation of Neurotransmitter Release by Human Endosulfine A or B

The ability of endosulfine to modulate the release of a variety of neurotransmitters including but not limited to dopamine and acetylcholine can be determined in tissue slices or synaptosomal preparations prepared from mammalian tissues. The example provided herein details a method for measuring dopamine release from rat striatal slices. It is understood that one of ordinary skill in the art may utilize a similar methodology to assess the release of other neurotransmitters including acetylcholine, serotonin, noradrenaline and histamine.

A. Stimulation of Striatal [$^3$H]Dopamine Release by Endosulfine A and B

Endosulfine A and/or endosulfine B evoked release of [ring-2,5,6-$^3$H]dopamine (24.4 Ci/mmol) is measured in superfused rat striatal slices. Striata are dissected from two male Sprague-Dawley rats and sliced 0.35×0.25 mm by a MoIlwain Tissue Chopper (Brinkman Instrument Co., Westbury, N.Y.). After two washes with Krebs-HEPES buffer (137 mM NaCl, 4.7 mM KCl, 1 mM $MgSO_4$, 2.5 mM $CaCl_2$, 1.25 mM $NaH_2PO_4$, 10 mM glucose, 15 mM HEPES-NaOH, pH 7.4), containing 10 μM pargyline and 10 μM ascorbic acid, slices are preincubated for 10 min at 37° C. under 95%/5% $O_2/CO_2$. After replacing the buffer, slices are labeled with 100 nM [$^3$H]dopamine for 25 min in Krebs-HEPES at 37° C. Aliquots of slices are placed in 18 superfusion chambers of a Brandel SP2000 superfusion apparatus (Brandel, Gaithersberg, Md.). Following 47 min of washout, slices are exposed to endosulfine A and/or endosulfine B (1 pM to 100 μM) for 4 min. Collected fractions are counted in 5 mL of scintillation fluid. Tissue is recovered from superfusion chambers, solubilized with 1 mL of Solvable™ (DuPont-NEN, Boston, Mass.) and counted in 15 mL of scintillation fluid.

Fractional release of [$^3$H]dopamine is calculated from radioactivity above baseline as a fraction of total radioactivity. Relative potencies are calculated using the release evoked by 100 nM (−)-nicotine as a standard. $EC_{50}$ values are determined by non-linear least squares regression analysis using Inplo™ (GraphPad Software, Inc., San Diego, Calif.).

B. Inhibition of Potassium-Evoked [$^3$H]Dopamine Release by Endosulfine A and B Potassium evoked release of [ring-2,5,6-$^3$H]dopamine (24.4 Ci/mmol) is measured in superfused rat striatal slices. Striata are dissected from two male Sprague-Dawley rats and sliced 0.35×0.25 mm by a McIlwain Tissue Chopper (Brinkman Instrument Co., Westbury, N.Y.). After two washes with Krebs-HEPES buffer (137 mM NaCl, 4.7 mM KCl, 1 mM $MgSO_4$, 2.5 mM $CaCl_2$, 1.25 mM $NaH_2PO_4$, 10 mM glucose, 15 mM HEPES-NaOH, pH 7.4), containing 10 μM pargyline and 10 μM ascorbic acid, slices are preincubated for 10 min at 37° C. under 95%/5% $O_2/CO_2$. After replacing the buffer, slices are labeled with 100 nM [$^3$H] dopamine for 25 min in Krebs-HEPES at 37° C. Aliquots of slices are placed in 18 superfusion chambers of a Brandel SP2000 superfusion apparatus (Brandel, Gaithersberg, Md.). Following 47 min of washout, slices are exposed to 20 mM potassium. To assess the inhibitory effects of endosulfine, endosulfine A (1 pM to 100 μM) and/or endosulfine B (1 pM to 100 μM) is added to the chambers 10 prior to the 20 mM potassium. Collected fractions are counted in 5 mL of scintillation fluid. Tissue is recovered from superfusion chambers, solubilized with 1 mL of Solvable™ (DuPont-NEN) and counted in 15 mL of scintillation fluid.

Fractional release of [$^3$H]dopamine is calculated from radioactivity above baseline as a fraction of total radioactivity. Relative potencies were calculated using the release evoked by 100 nM (−)-nicotine as a standard. $EC_{50}$ values were determined by non-linear least squares regression analysis using Inplot™ (GraphPad Software, Inc., San Diego, Calif.).

It is understood that the conditions and reagents under which the procedure is performed may be optimized or altered.

Example 16

Modulation of Cardiovascular Properties by Endosulfines

ATP-dependent potassium channel activators confer protection from damage resulting from ischemia and reperfusion in the heart and also modulate hemodynamic variables. The recent finding that SUR 2A is selectively expressed in heart raises the possibility that an endosulfine selectively expressed in heart tissue may play a role in setting and modulating cardiac hemodynamics and may offer an alternate approach to the treatment of cardiac ischemia. Methodology to evaluate the regional hemodynamic effects of endosulfine in rats instrumented to simultaneously measure blood flow in the coronary, renal, mesenteric and hindquarters vascular beds allows the effects of endosulfines on cardiovascular function to be assessed.

Instrumentation: All experiments are conducted in accordance with a protocol approved by the Abbott Laboratories Animal Care and Use Committee and conform to the NIH Guidelines for the Use and Care of Laboratory Animals. Male Sprague-Dawley rats, 350 to 400 g, are anesthetized with 100 mg/kg IP Inactin (BYK-Gulden) and instrumented as follows: Catheters are inserted into the femoral artery and vein for the measurement of arterial pressure and administration of compounds, respectively. A tracheotomy is performed to ensure airway patency and to allow for mechanical positive pressure ventilation. The animal is then placed on a ventilator at 1 mL room air per 100 gm body weight at 60 cycles/min.

The heart is exposed via an intercostal approach and the pericardium is gently dissected. A suction-cup type miniature pulsed-Doppler probe is then placed on the myocardium above the left main coronary artery. Via a midline abdominal incision, the right renal and superior mesenteric artery and the abdominal aorta are exposed. Cuff-type miniature pulsed-Doppler flow probes are then placed on each vessel for the measurement of renal, mesenteric and hindquarters blood flow, respectively. The incision is closed with 8 mm wound clips and the animal is allowed to stabilize for 30–45 min.

Arterial pressure and Doppler shifts from each of the 4 vascular beds are recorded on a polygraph. Computerized data acquisition from arterial pressure and blood flows yields the following measured parameters: mean arterial pressure, heart rate, and blood flow. These values are collected every five seconds throughout the experiments. Blood flow and resistance measurements are expressed as percent change from control or percent of control.

The animals are then allowed to stabilize to 30 to 45 min. After stabilization, endosulfine is administered and the regional hemodynamic effects of endosulfine are determined by the methods disclosed hereinabove.

It is understood that the conditions for performing the methodology to evaluate the regional hemodynamic effects of endosulfine can be optimized depending on the test animal.

Example 17

Inhibition of Endogenous Endosulfine Expression

Antisense RNA or DNA is a strategy currently widely used to reduce or completely block the endogenous synthesis of proteins. The antisense molecule can be an oligonucleotide targeted to a particular region of the endogenous message, or can be transcribed from an expression vector in which the cDNA for the target gene is ligated in the antisense orientation. In the case of endosulfine, an antisense molecule targeted to the translation initiation site is predicted to inhibit the synthesis of both the endosulfine A and B isoforms. Oligonucleotides targeted to the 3' UTR can be used to selectively inhibit the synthesis of endosulfine A or B. The oligonucleotide of interest is added directly into the medium of cultured cells. As a first step, a range concentration from 1 mM to 1 mM is tested. After different times of exposure to the antisense (from 10 hours to 5 days), the synthesis and steady-state levels of the endosulfine is assessed by immunoblot with an endosulfine-specific antibody (see Example 10). Once the optimal concentration and time of exposures have been established, the effect of this reduction of endosulfine synthesis are analyzed in biological assays such as rubidium flux, neuroprotection insulin secretion, neurotransmitter release, and modulation of cardiovascular properties (see Examples 12–16).

We claim:

1. An isolated or purified polynucleotide which encodes a human endosulfine wherein said polynucleotide comprises a sequence selected from the group consisting of:
   (a) a polynucleotide of SEQ ID NO:1;
   (b) a polynucleotide of SEQ ID NO:2;
   (c) a polynucleotide comprising from about nucleotide position 107 to about nucleotide position 460 of SEQ ID NO:1;
   (d) a polynucleotide comprising from about nucleotide position 107 to about nucleotide position 472 of SEQ ID NO:2;
   (e) a polynucleotide encoding a polypeptide having the amino acid sequence of SEQ ID NO:3;
   (f) a polynucleotide encoding a polypeptide having the amino acid sequence of SEQ ID NO:4; and
   (g) a polynucleotide which is fully complementary to the polynucleotide of (a), (b), (c), (d), (e) or (f).

2. A recombinant expression vector comprising the polynucleotide of claim 1.

3. The recombinant expression vector of claim 2 wherein the expression vector is selected from the group consisting of pProEx1 and pcDNA3.1.

4. A host cell transformed with the expression vector of claim 2.

5. The host cell of claim 4 wherein said host cell is a prokaryotic cell or eukaryotic cell.

6. A method for producing a polypeptide containing at feast one human endosulfine epitope comprising incubating host cells transformed with an expression vector wherein said expression vector comprises a polynucleotide sequence which encodes a human endosulfine, and producing said polypeptide, wherein said polynucleotide sequence comprises a sequence selected from the group consisting of:
   (a) a polynucleotide of SEQ ID NO: 1;
   (b) a polynucleotide of SEQ ID NO:2;
   (c) a polynucleotide comprising from about nucleotide position 107 to about nucleotide position 460 of SEQ ID NO: 1;
   (d) a polynucleotide comprising from about nucleotide position 107 to about nucleotide position 472 of SEQ ID NO:2;
   (e) a polynucleotide encoding the polypeptide having the amino acid sequence of SEQ ID NO:3;
   (f) a polynucleotide encoding the polypeptide having the amino acid sequence of SEQ ID NO:4; and
   (g) a polynucleotide which is fully complementary to the polynucleotide of (a), (b), (c), (d), (e) or (f).

* * * * *